(12) United States Patent
Chang et al.

(10) Patent No.: US 11,839,410 B2
(45) Date of Patent: Dec. 12, 2023

(54) MAGNETIC IMPLANTS WITH IMPROVED ANATOMICAL COMPATIBILITY

(71) Applicant: NuVasive Specialized Orthopedics, Inc., San Diego, CA (US)

(72) Inventors: Arvin Chang, Yorba Linda, CA (US); Blair Walker, Mission Viejo, CA (US); Scott Pool, Laguna Hills, CA (US); Peter P. Tran, Irvine, CA (US)

(73) Assignee: Nuvasive Inc., San Diego, CA (US)

( * ) Notice: Subject to any disclaimer, the term of this patent is extended or adjusted under 35 U.S.C. 154(b) by 503 days.

(21) Appl. No.: 16/748,605

(22) Filed: Jan. 21, 2020

(65) Prior Publication Data

US 2020/0155201 A1    May 21, 2020

Related U.S. Application Data

(63) Continuation of application No. 13/525,058, filed on Jun. 15, 2012, now abandoned.

(51) Int. Cl.
*A61B 17/70* (2006.01)

(52) U.S. Cl.
CPC .................. *A61B 17/7017* (2013.01)

(58) Field of Classification Search
CPC ............ A61B 17/7016; A61B 17/7216; A61B 17/7225; A61B 17/7014
See application file for complete search history.

(56) References Cited

U.S. PATENT DOCUMENTS

| | | |
|---|---|---|
| 2,702,031 A | 2/1955 | Wenger |
| 3,111,945 A | 11/1963 | Von Solbrig |
| 3,372,476 A | 3/1968 | Peiffer |
| 3,377,576 A | 4/1968 | Langberg |
| 3,512,901 A | 5/1970 | Law |

(Continued)

FOREIGN PATENT DOCUMENTS

| | | |
|---|---|---|
| CA | 2655093 A1 | 12/2007 |
| CN | 1697630 A | 11/2005 |

(Continued)

OTHER PUBLICATIONS

Abe et al., "Experimental external fixation combined with percutaneous discectomy in the management of scoliosis.", SPINE, 1999, pp. 646-653, 24, No. 7.

(Continued)

*Primary Examiner* — Jan Christopher L Merene

(57) ABSTRACT

A distraction system includes a first distraction device having a first adjustable portion and a first distraction rod configured to telescope within the first adjustable portion, the first adjustable portion having contained therein a first rotatable magnetic assembly mechanically coupled to a first screw configured to axially telescope the first distraction rod. A second distraction device is provided and includes a second adjustable portion and a second distraction rod configured to telescope within the second adjustable portion, the second adjustable portion having contained therein a second rotatable magnetic assembly mechanically coupled to a second screw configured to axially telescope the second distraction rod. An adjustable joint connects one end of the first adjustable portion to one end of the second adjustable portion.

17 Claims, 15 Drawing Sheets

(56) References Cited

U.S. PATENT DOCUMENTS

| | | |
|---|---|---|
| 3,597,781 A | 8/1971 | Eibes |
| 3,810,259 A | 5/1974 | Summers |
| 3,900,025 A | 8/1975 | Barnes, Jr. |
| 3,915,151 A | 10/1975 | Kraus |
| RE28,907 E | 7/1976 | Eibes et al. |
| 3,976,060 A | 8/1976 | Hildebrandt et al. |
| 4,010,758 A | 3/1977 | Rockland et al. |
| 4,056,743 A | 11/1977 | Clifford et al. |
| 4,068,821 A | 1/1978 | Morrison |
| 4,078,559 A | 3/1978 | Nissinen |
| 4,204,541 A | 5/1980 | Kapitanov |
| 4,357,946 A | 11/1982 | Dutcher et al. |
| 4,386,603 A | 6/1983 | Mayfield |
| 4,448,191 A | 5/1984 | Rodnyansky et al. |
| 4,486,176 A | 12/1984 | Tardieu et al. |
| 4,501,266 A | 2/1985 | McDaniel |
| 4,522,501 A | 6/1985 | Shannon |
| 4,537,520 A | 8/1985 | Ochiai et al. |
| 4,550,279 A | 10/1985 | Klein |
| 4,561,798 A | 12/1985 | Elcrin et al. |
| 4,573,454 A | 3/1986 | Hoffman |
| 4,592,355 A | 6/1986 | Antebi |
| 4,595,007 A | 6/1986 | Mericle |
| 4,642,257 A | 2/1987 | Chase |
| 4,658,809 A | 4/1987 | Ulrich et al. |
| 4,700,091 A | 10/1987 | Wuthrich |
| 4,747,832 A | 5/1988 | Buffet |
| 4,854,304 A | 8/1989 | Zielke |
| 4,895,141 A | 1/1990 | Koeneman |
| 4,904,861 A | 2/1990 | Epstein et al. |
| 4,931,055 A | 6/1990 | Bumpus et al. |
| 4,940,467 A | 7/1990 | Tronzo |
| 4,957,495 A | 9/1990 | Kluger |
| 4,973,331 A | 11/1990 | Pursley et al. |
| 5,010,879 A | 4/1991 | Moriya et al. |
| 5,030,235 A | 7/1991 | Campbell, Jr. |
| 5,041,112 A | 8/1991 | Mingozzi et al. |
| 5,064,004 A | 11/1991 | Lundell |
| 5,074,882 A | 12/1991 | Grammont et al. |
| 5,092,889 A | 3/1992 | Campbell, Jr. |
| 5,094,247 A * | 3/1992 | Hernandez ............ A61B 10/06 600/564 |
| 5,133,716 A | 7/1992 | Plaza |
| 5,142,407 A | 8/1992 | Varaprasad et al. |
| 5,156,605 A | 10/1992 | Pursley et al. |
| 5,261,908 A | 11/1993 | Campbell, Jr. |
| 5,263,955 A | 11/1993 | Baumgart et al. |
| 5,290,289 A | 3/1994 | Sanders et al. |
| 5,306,275 A | 4/1994 | Bryan |
| 5,330,503 A | 7/1994 | Yoon |
| 5,334,202 A | 8/1994 | Carter |
| 5,336,223 A | 8/1994 | Rogers |
| 5,356,411 A | 10/1994 | Spievack |
| 5,356,424 A | 10/1994 | Buzerak et al. |
| 5,364,396 A | 11/1994 | Robinson et al. |
| 5,403,322 A | 4/1995 | Herzenberg et al. |
| 5,429,638 A | 7/1995 | Muschler et al. |
| 5,437,266 A | 8/1995 | McPherson et al. |
| 5,466,261 A | 11/1995 | Richelsoph |
| 5,468,030 A | 11/1995 | Walling |
| 5,480,437 A | 1/1996 | Draenert |
| 5,487,743 A | 1/1996 | Laurain |
| 5,509,888 A | 4/1996 | Miller |
| 5,516,335 A | 5/1996 | Kummer et al. |
| 5,527,309 A | 6/1996 | Shelton |
| 5,536,269 A | 7/1996 | Spievack |
| 5,549,610 A | 8/1996 | Russell et al. |
| 5,573,012 A | 11/1996 | McEwan |
| 5,575,790 A | 11/1996 | Chen et al. |
| 5,582,616 A | 12/1996 | Bolduc et al. |
| 5,620,445 A | 4/1997 | Brosnahan et al. |
| 5,620,449 A | 4/1997 | Faccioli et al. |
| 5,626,579 A | 5/1997 | Muschler et al. |
| 5,626,613 A | 5/1997 | Schmieding |
| 5,632,744 A | 5/1997 | Campbell, Jr. |
| 5,659,217 A | 8/1997 | Petersen |
| 5,662,650 A | 9/1997 | Bailey |
| 5,662,683 A | 9/1997 | Kay |
| 5,667,507 A | 9/1997 | Corin |
| 5,672,175 A | 9/1997 | Martin |
| 5,672,177 A | 9/1997 | Seldin |
| 5,700,263 A | 12/1997 | Schendel |
| 5,704,938 A | 1/1998 | Staehlin et al. |
| 5,704,939 A | 1/1998 | Justin |
| 5,720,746 A | 2/1998 | Soubeiran |
| 5,743,910 A | 4/1998 | Bays et al. |
| 5,752,955 A | 5/1998 | Errico |
| 5,762,599 A | 6/1998 | Sohn |
| 5,771,903 A | 6/1998 | Jakobsson |
| 5,800,434 A | 9/1998 | Campbell, Jr. |
| 5,810,815 A | 9/1998 | Morales |
| 5,827,286 A | 10/1998 | Incavo et al. |
| 5,830,221 A | 11/1998 | Stein et al. |
| 5,879,375 A | 3/1999 | Larson, Jr. et al. |
| 5,902,304 A | 5/1999 | Walker et al. |
| 5,935,127 A | 8/1999 | Border |
| 5,945,762 A | 8/1999 | Chen et al. |
| 5,961,553 A | 10/1999 | Coty et al. |
| 5,976,138 A | 11/1999 | Baumgart et al. |
| 5,979,456 A | 11/1999 | Magovern |
| 6,022,349 A | 2/2000 | McLeod et al. |
| 6,033,412 A | 3/2000 | Losken et al. |
| 6,034,296 A | 3/2000 | Elvin et al. |
| 6,074,882 A | 6/2000 | Eckardt |
| 6,102,922 A | 8/2000 | Jakobsson et al. |
| 6,106,525 A | 8/2000 | Sachse |
| 6,126,660 A | 10/2000 | Dietz |
| 6,126,661 A | 10/2000 | Faccioli et al. |
| 6,138,681 A | 10/2000 | Chen et al. |
| 6,139,316 A | 10/2000 | Sachdeva et al. |
| 6,162,223 A | 12/2000 | Orsak et al. |
| 6,183,476 B1 | 2/2001 | Gerhardt et al. |
| 6,200,317 B1 | 3/2001 | Aalsma et al. |
| 6,234,956 B1 | 5/2001 | He et al. |
| 6,238,396 B1 | 5/2001 | Lombardo |
| 6,241,730 B1 | 6/2001 | Alby |
| 6,245,075 B1 | 6/2001 | Betz et al. |
| 6,315,784 B1 | 11/2001 | Djurovic |
| 6,319,255 B1 | 11/2001 | Grundei et al. |
| 6,331,744 B1 | 12/2001 | Chen et al. |
| 6,336,929 B1 | 1/2002 | Justin |
| 6,343,568 B1 | 2/2002 | McClasky |
| 6,358,283 B1 | 3/2002 | Hogfors et al. |
| 6,375,682 B1 | 4/2002 | Fleischmann et al. |
| 6,389,187 B1 | 5/2002 | Greenaway et al. |
| 6,400,980 B1 | 6/2002 | Lemelson |
| 6,402,753 B1 | 6/2002 | Cole et al. |
| 6,409,175 B1 | 6/2002 | Evans et al. |
| 460,184 A1 | 7/2002 | Schendel et al. |
| 6,416,516 B1 | 7/2002 | Stauch et al. |
| 6,417,750 B1 | 7/2002 | Sohn |
| 6,499,907 B1 | 12/2002 | Baur |
| 6,500,110 B1 | 12/2002 | Davey et al. |
| 6,508,820 B2 | 1/2003 | Bales |
| 6,510,345 B1 | 1/2003 | Van Bentem |
| 6,537,196 B1 | 3/2003 | Creighton, IV et al. |
| 6,554,831 B1 | 4/2003 | Rivard et al. |
| 6,565,573 B1 | 5/2003 | Ferrante et al. |
| 6,565,576 B1 | 5/2003 | Stauch et al. |
| 6,582,313 B2 | 6/2003 | Perrow |
| 6,583,630 B2 | 6/2003 | Mendes et al. |
| 6,616,669 B2 | 9/2003 | Ogilvie et al. |
| 6,626,917 B1 | 9/2003 | Craig |
| 6,656,135 B2 | 12/2003 | Zogbi et al. |
| 6,656,194 B1 | 12/2003 | Gannoe et al. |
| 6,667,725 B1 | 12/2003 | Simons et al. |
| 6,673,079 B1 | 1/2004 | Kane |
| 6,702,816 B2 | 3/2004 | Buhler |
| 6,706,042 B2 | 3/2004 | Taylor |
| 6,709,293 B2 | 3/2004 | Mori et al. |
| 6,730,087 B1 | 5/2004 | Butsch |
| 6,761,503 B2 | 7/2004 | Breese |
| 6,765,330 B2 | 7/2004 | Baur |
| 6,769,499 B2 | 8/2004 | Cargill et al. |

(56) References Cited

U.S. PATENT DOCUMENTS

| | | |
|---|---|---|
| 6,789,442 B2 | 9/2004 | Forch |
| 6,796,984 B2 | 9/2004 | Soubeiran |
| 6,802,844 B2 | 10/2004 | Ferree |
| 6,809,434 B1 | 10/2004 | Duncan et al. |
| 6,835,207 B2 | 12/2004 | Zacouto et al. |
| 6,849,076 B2 | 2/2005 | Blunn |
| 6,852,113 B2 | 2/2005 | Nathanson et al. |
| 6,918,838 B2 | 7/2005 | Schwarzler et al. |
| 6,918,910 B2 | 7/2005 | Smith et al. |
| 6,921,400 B2 | 7/2005 | Sohngen |
| 6,923,951 B2 | 8/2005 | Contag et al. |
| 6,971,143 B2 | 12/2005 | Domroese |
| 7,001,346 B2 | 2/2006 | White |
| 7,008,425 B2 | 3/2006 | Phillips |
| 7,011,658 B2 | 3/2006 | Young |
| 7,029,472 B1 | 4/2006 | Fortin |
| 7,029,475 B2 | 4/2006 | Panjabi |
| 7,041,105 B2 | 5/2006 | Michelson |
| 7,060,080 B2 | 6/2006 | Bachmann |
| 7,063,706 B2 | 6/2006 | Wittenstein |
| 7,105,029 B2 | 9/2006 | Doubler et al. |
| 7,105,968 B2 | 9/2006 | Nissen |
| 7,114,501 B2 | 10/2006 | Johnson et al. |
| 7,115,129 B2 | 10/2006 | Heggeness |
| 7,135,022 B2 | 11/2006 | Kosashvili et al. |
| 7,160,312 B2 | 1/2007 | Saadat |
| 7,163,538 B2 | 1/2007 | Altarac et al. |
| 7,189,005 B2 | 3/2007 | Ward |
| 7,191,007 B2 | 3/2007 | Desai et al. |
| 7,218,232 B2 | 5/2007 | DiSilvestro et al. |
| 7,238,191 B2 | 7/2007 | Bachmann |
| 7,241,300 B2 | 7/2007 | Sharkawy et al. |
| 7,243,719 B2 | 7/2007 | Baron et al. |
| 7,255,682 B1 | 8/2007 | Bartol, Jr. et al. |
| 7,282,023 B2 | 10/2007 | Frering |
| 7,285,087 B2 | 10/2007 | Moaddeb et al. |
| 7,302,015 B2 | 11/2007 | Kim et al. |
| 7,302,858 B2 | 12/2007 | Walsh et al. |
| 7,314,443 B2 | 1/2008 | Jordan et al. |
| 7,333,013 B2 | 2/2008 | Berger |
| 7,357,037 B2 | 4/2008 | Hnat et al. |
| 7,357,635 B2 | 4/2008 | Belfor et al. |
| 7,360,542 B2 | 4/2008 | Nelson et al. |
| 7,390,007 B2 | 6/2008 | Helms et al. |
| 7,390,294 B2 | 6/2008 | Hassler, Jr. |
| 7,402,134 B2 | 7/2008 | Moaddeb et al. |
| 7,402,176 B2 | 7/2008 | Malek |
| 7,429,259 B2 | 9/2008 | Cadeddu et al. |
| 7,445,010 B2 | 11/2008 | Kugler et al. |
| 7,458,981 B2 | 12/2008 | Fielding et al. |
| 7,485,149 B1 | 2/2009 | White |
| 7,489,495 B2 | 2/2009 | Stevenson |
| 7,530,981 B2 | 5/2009 | Kutsenko |
| 7,531,002 B2 | 5/2009 | Sutton et al. |
| 7,553,298 B2 | 6/2009 | Hunt et al. |
| 7,561,916 B2 | 7/2009 | Hunt et al. |
| 7,601,156 B2 | 10/2009 | Robinson |
| 7,611,526 B2 | 11/2009 | Carl et al. |
| 7,618,435 B2 | 11/2009 | Opolski |
| 7,658,754 B2 | 2/2010 | Zhang et al. |
| 7,666,184 B2 | 2/2010 | Stauch |
| 7,666,210 B2 | 2/2010 | Franck et al. |
| 7,678,136 B2 | 3/2010 | Doubler et al. |
| 7,678,139 B2 | 3/2010 | Garamszegi et al. |
| 7,708,737 B2 | 5/2010 | Kraft et al. |
| 7,708,762 B2 | 5/2010 | McCarthy et al. |
| 7,727,143 B2 | 6/2010 | Birk et al. |
| 7,753,913 B2 | 7/2010 | Szakelyhidi, Jr. et al. |
| 7,753,915 B1 | 7/2010 | Eksler et al. |
| 7,762,998 B2 | 7/2010 | Birk et al. |
| 7,763,080 B2 | 7/2010 | Southworth |
| 7,766,855 B2 | 8/2010 | Miethke |
| 7,775,215 B2 | 8/2010 | Hassler, Jr. et al. |
| 7,776,068 B2 | 8/2010 | Ainsworth et al. |
| 7,776,075 B2 | 8/2010 | Bruneau et al. |
| 7,776,091 B2 | 8/2010 | Mastrorio |
| 7,787,958 B2 | 8/2010 | Stevenson |
| 7,794,476 B2 | 9/2010 | Wisnewski |
| 7,811,328 B2 | 10/2010 | Molz, IV et al. |
| 7,835,779 B2 | 11/2010 | Anderson et al. |
| 7,837,691 B2 | 11/2010 | Cordes et al. |
| 7,862,502 B2 | 1/2011 | Pool et al. |
| 7,862,586 B2 | 1/2011 | Malek |
| 7,867,235 B2 | 1/2011 | Fell et al. |
| 7,875,033 B2 | 1/2011 | Richter et al. |
| 7,887,566 B2 | 2/2011 | Hynes |
| 7,901,381 B2 | 3/2011 | Birk et al. |
| 7,909,852 B2 | 3/2011 | Boomer et al. |
| 7,918,844 B2 | 4/2011 | Byrum et al. |
| 7,938,841 B2 | 5/2011 | Sharkawy et al. |
| 7,955,357 B2 | 6/2011 | Kiester |
| 7,981,025 B2 | 7/2011 | Pool et al. |
| 7,985,256 B2 | 7/2011 | Grotz et al. |
| 7,988,709 B2 | 8/2011 | Clark et al. |
| 8,002,809 B2 | 8/2011 | Baynham |
| 8,011,308 B2 | 9/2011 | Picchio |
| 8,034,080 B2 | 10/2011 | Malandain et al. |
| 8,043,299 B2 | 10/2011 | Conway |
| 8,043,338 B2 | 10/2011 | Dant |
| 8,057,472 B2 | 11/2011 | Walker et al. |
| 8,057,473 B2 | 11/2011 | Orsak et al. |
| 8,057,513 B2 | 11/2011 | Kohm et al. |
| 8,083,741 B2 | 12/2011 | Morgan et al. |
| 8,092,499 B1 | 1/2012 | Roth |
| 8,095,317 B2 | 1/2012 | Ekseth et al. |
| 8,105,360 B1 | 1/2012 | Connor |
| 8,105,363 B2 | 1/2012 | Fielding |
| 8,114,158 B2 | 2/2012 | Carl et al. |
| 8,123,805 B2 | 2/2012 | Makower et al. |
| 8,133,280 B2 | 3/2012 | Voellmicke et al. |
| 8,147,517 B2 | 4/2012 | Trieu |
| 8,147,549 B2 | 4/2012 | Metcalf, Jr. et al. |
| 8,162,897 B2 | 4/2012 | Byrum |
| 8,162,979 B2 | 4/2012 | Sachs et al. |
| 8,177,789 B2 | 5/2012 | Magill et al. |
| 8,197,490 B2 | 6/2012 | Pool et al. |
| 8,211,149 B2 | 7/2012 | Justis |
| 8,211,151 B2 | 7/2012 | Schwab et al. |
| 8,211,179 B2 | 7/2012 | Molz, IV |
| 8,216,275 B2 | 7/2012 | Fielding |
| 8,221,420 B2 | 7/2012 | Keller |
| 8,226,690 B2 | 7/2012 | Altarac et al. |
| 8,236,002 B2 | 8/2012 | Fortin et al. |
| 8,241,331 B2 | 8/2012 | Arnin |
| 8,246,533 B2 | 8/2012 | Chang et al. |
| 8,246,630 B2 | 8/2012 | Manzi et al. |
| 8,252,063 B2 | 8/2012 | Stauch |
| 8,267,969 B2 | 9/2012 | Altarac et al. |
| 8,278,941 B2 | 10/2012 | Kroh et al. |
| 8,282,671 B2 | 10/2012 | Connor |
| 8,298,240 B2 | 10/2012 | Giger |
| 8,323,290 B2 | 12/2012 | Metzger et al. |
| 8,357,182 B2 | 1/2013 | Seme |
| 8,366,628 B2 | 2/2013 | Denker et al. |
| 8,372,078 B2 | 2/2013 | Collazo |
| 8,386,018 B2 | 2/2013 | Stauch et al. |
| 8,394,124 B2 | 3/2013 | Biyani |
| 8,403,958 B2 | 3/2013 | Schwab |
| 8,414,584 B2 | 4/2013 | Brigido |
| 8,419,801 B2 | 4/2013 | Disilvestro |
| 8,425,608 B2 | 4/2013 | Dewey et al. |
| 8,435,268 B2 | 5/2013 | Thompson et al. |
| 8,439,915 B2 | 5/2013 | Harrison |
| 8,439,926 B2 | 5/2013 | Bojarski et al. |
| 8,444,693 B2 | 5/2013 | Reiley |
| 8,469,908 B2 | 6/2013 | Asfora |
| 8,470,004 B2 | 6/2013 | Reiley |
| 8,480,712 B1 | 7/2013 | Samuel |
| 8,486,070 B2 | 7/2013 | Morgan et al. |
| 8,486,076 B2 | 7/2013 | Chavarria et al. |
| 8,486,110 B2 | 7/2013 | Fielding |
| 8,486,147 B2 | 7/2013 | De Villiers et al. |
| 8,494,805 B2 | 7/2013 | Roche et al. |
| 8,496,662 B2 | 7/2013 | Novak et al. |

(56) References Cited

U.S. PATENT DOCUMENTS

| | | |
|---|---|---|
| 8,518,062 B2 | 8/2013 | Cole et al. |
| 8,523,866 B2 | 9/2013 | Sidebotham et al. |
| 8,529,474 B2 | 9/2013 | Gupta et al. |
| 8,529,606 B2 | 9/2013 | Alamin et al. |
| 8,529,607 B2 | 9/2013 | Alamin et al. |
| 8,556,901 B2 | 10/2013 | Anthony et al. |
| 8,556,911 B2 | 10/2013 | Mehta et al. |
| 8,556,975 B2 | 10/2013 | Ciupik et al. |
| 8,562,653 B2 | 10/2013 | Alamin et al. |
| 8,568,457 B2 | 10/2013 | Hunziker |
| 8,617,220 B2 | 10/2013 | Skaggs |
| 8,579,979 B2 | 11/2013 | Edie et al. |
| 8,585,595 B2 | 11/2013 | Heilman |
| 8,585,740 B1 | 11/2013 | Ross et al. |
| 8,591,549 B2 | 11/2013 | Lange |
| 8,591,553 B2 | 11/2013 | Eisermann et al. |
| 8,613,758 B2 | 12/2013 | Linares |
| 8,623,036 B2 | 1/2014 | Harrison et al. |
| 8,632,544 B2 | 1/2014 | Haaja et al. |
| 8,632,548 B2 | 1/2014 | Soubeiran |
| 8,632,563 B2 | 1/2014 | Nagase et al. |
| 8,636,771 B2 | 1/2014 | Butler et al. |
| 8,636,802 B2 | 1/2014 | Serhan et al. |
| 8,641,719 B2 | 2/2014 | Gephart et al. |
| 8,641,723 B2 | 2/2014 | Connor |
| 8,657,856 B2 | 2/2014 | Gephart et al. |
| 8,663,285 B2 | 3/2014 | Dall et al. |
| 8,663,287 B2 | 3/2014 | Butler et al. |
| 8,668,719 B2 | 3/2014 | Alamin et al. |
| 8,709,090 B2 | 4/2014 | Makower et al. |
| 8,758,347 B2 | 6/2014 | Weiner et al. |
| 8,758,355 B2 | 6/2014 | Fisher et al. |
| 8,771,272 B2 | 7/2014 | LeCronier et al. |
| 8,777,947 B2 | 7/2014 | Zahrly et al. |
| 8,777,995 B2 | 7/2014 | McClintock et al. |
| 8,790,343 B2 | 7/2014 | McClellan et al. |
| 8,790,409 B2 | 7/2014 | Van den Heuvel et al. |
| 8,828,058 B2 | 9/2014 | Elsebaie et al. |
| 8,828,087 B2 | 9/2014 | Stone et al. |
| 8,840,651 B2 | 9/2014 | Reiley |
| 8,870,881 B2 | 10/2014 | Rezach et al. |
| 8,870,959 B2 | 10/2014 | Arnin |
| 8,894,663 B2 | 11/2014 | Giger |
| 8,915,915 B2 | 12/2014 | Harrison et al. |
| 8,915,917 B2 | 12/2014 | Doherty et al. |
| 8,920,422 B2 | 12/2014 | Homeier et al. |
| 8,945,188 B2 | 2/2015 | Rezach et al. |
| 8,961,521 B2 | 2/2015 | Keefer et al. |
| 8,961,567 B2 | 2/2015 | Hunziker |
| 8,968,402 B2 | 3/2015 | Myers et al. |
| 8,968,406 B2 | 3/2015 | Arnin |
| 8,992,527 B2 | 3/2015 | Guichet |
| 9,022,917 B2 | 5/2015 | Kasic et al. |
| 9,044,218 B2 | 6/2015 | Young |
| 9,060,810 B2 | 6/2015 | Kercher et al. |
| 9,078,703 B2 | 7/2015 | Arnin |
| 9,198,696 B1 | 12/2015 | Bannigan |
| 2002/0050112 A1 | 5/2002 | Koch et al. |
| 2002/0072758 A1 | 6/2002 | Reo et al. |
| 2002/0164905 A1 | 11/2002 | Bryant |
| 2003/0040671 A1 | 2/2003 | Somogyi et al. |
| 2003/0144669 A1 | 7/2003 | Robinson |
| 2003/0187432 A1 | 10/2003 | Johnson |
| 2003/0220643 A1 | 11/2003 | Ferree |
| 2003/0220644 A1 | 11/2003 | Thelen et al. |
| 2004/0011137 A1 | 1/2004 | Hnat et al. |
| 2004/0011365 A1 | 1/2004 | Govari et al. |
| 2004/0019353 A1 | 1/2004 | Freid et al. |
| 2004/0023623 A1 | 2/2004 | Stauch et al. |
| 2004/0030395 A1* | 2/2004 | Blunn ............... A61B 17/7016 623/23.45 |
| 2004/0055610 A1 | 3/2004 | Forsell |
| 2004/0133219 A1 | 7/2004 | Forsell |
| 2004/0138725 A1 | 7/2004 | Forsell |
| 2004/0193266 A1 | 9/2004 | Meyer |
| 2004/0225323 A1 | 11/2004 | Nagase |
| 2005/0034705 A1 | 2/2005 | McClendon |
| 2005/0049617 A1 | 3/2005 | Chatlynne et al. |
| 2005/0055025 A1 | 3/2005 | Zacouto |
| 2005/0065529 A1 | 3/2005 | Liu et al. |
| 2005/0090823 A1 | 4/2005 | Bartimus |
| 2005/0159754 A1 | 7/2005 | Odrich |
| 2005/0228376 A1 | 10/2005 | Boomer |
| 2005/0234448 A1 | 10/2005 | McCarthy |
| 2005/0234462 A1 | 10/2005 | Hershberger |
| 2005/0246034 A1 | 11/2005 | Soubeiran |
| 2005/0251109 A1 | 11/2005 | Soubeiran |
| 2005/0261779 A1 | 11/2005 | Meyer |
| 2005/0272976 A1 | 12/2005 | Tanaka et al. |
| 2006/0004459 A1 | 1/2006 | Hazebrouck et al. |
| 2006/0009767 A1 | 1/2006 | Kiester |
| 2006/0036259 A1 | 2/2006 | Carl et al. |
| 2006/0036323 A1 | 2/2006 | Carl et al. |
| 2006/0036324 A1 | 2/2006 | Sachs et al. |
| 2006/0047282 A1 | 3/2006 | Gordon |
| 2006/0052782 A1 | 3/2006 | Morgan |
| 2006/0058792 A1 | 3/2006 | Hynes |
| 2006/0069447 A1 | 3/2006 | DiSilvestro et al. |
| 2006/0074448 A1 | 4/2006 | Harrison et al. |
| 2006/0079897 A1 | 4/2006 | Harrison et al. |
| 2006/0136062 A1 | 6/2006 | DiNello et al. |
| 2006/0142767 A1 | 6/2006 | Green et al. |
| 2006/0155279 A1 | 7/2006 | Ogilvie |
| 2006/0195087 A1 | 8/2006 | Sacher et al. |
| 2006/0195088 A1 | 8/2006 | Sacher et al. |
| 2006/0200134 A1 | 9/2006 | Freid et al. |
| 2006/0204156 A1 | 9/2006 | Takehara et al. |
| 2006/0235299 A1 | 10/2006 | Martinelli |
| 2006/0235424 A1 | 10/2006 | Vitale et al. |
| 2006/0241746 A1 | 10/2006 | Shaoulian et al. |
| 2006/0241767 A1 | 10/2006 | Doty |
| 2006/0249914 A1 | 11/2006 | Dulin |
| 2006/0271107 A1 | 11/2006 | Harrison et al. |
| 2006/0282073 A1 | 12/2006 | Simanovsky |
| 2006/0293683 A1 | 12/2006 | Stauch |
| 2007/0010814 A1 | 1/2007 | Stauch |
| 2007/0010887 A1 | 1/2007 | Williams et al. |
| 2007/0021644 A1 | 1/2007 | Woolson et al. |
| 2007/0031131 A1 | 2/2007 | Griffitts |
| 2007/0043376 A1 | 2/2007 | Leatherbury et al. |
| 2007/0050030 A1 | 3/2007 | Kim |
| 2007/0093844 A1* | 4/2007 | Dye ............... A61B 17/1668 606/84 |
| 2007/0118215 A1 | 5/2007 | Moaddeb |
| 2007/0149909 A1 | 6/2007 | Fortin |
| 2007/0161984 A1 | 7/2007 | Cresina et al. |
| 2007/0173833 A1 | 7/2007 | Butler |
| 2007/0173837 A1 | 7/2007 | Chan et al. |
| 2007/0179493 A1 | 8/2007 | Kim |
| 2007/0185374 A1 | 8/2007 | Kick et al. |
| 2007/0213751 A1 | 9/2007 | Scirica |
| 2007/0233090 A1 | 10/2007 | Naifeh |
| 2007/0233098 A1 | 10/2007 | Mastrorio et al. |
| 2007/0239159 A1 | 10/2007 | Altarac et al. |
| 2007/0239161 A1 | 10/2007 | Giger et al. |
| 2007/0255088 A1 | 11/2007 | Jacobson et al. |
| 2007/0264605 A1 | 11/2007 | Belfor |
| 2007/0265646 A1 | 11/2007 | McCoy |
| 2007/0270803 A1 | 11/2007 | Giger et al. |
| 2007/0276368 A1 | 11/2007 | Trieu et al. |
| 2007/0276369 A1 | 11/2007 | Allard et al. |
| 2007/0276373 A1 | 11/2007 | Malandain |
| 2007/0276378 A1 | 11/2007 | Harrison et al. |
| 2007/0276493 A1 | 11/2007 | Malandain et al. |
| 2007/0288024 A1 | 12/2007 | Gollogly |
| 2007/0288183 A1 | 12/2007 | Bulkes et al. |
| 2008/0009792 A1 | 1/2008 | Henniges et al. |
| 2008/0015577 A1 | 1/2008 | Loeb |
| 2008/0021454 A1 | 1/2008 | Chao et al. |
| 2008/0021455 A1 | 1/2008 | Chao et al. |
| 2008/0021456 A1 | 1/2008 | Gupta et al. |
| 2008/0027436 A1 | 1/2008 | Cournoyer |
| 2008/0033431 A1 | 2/2008 | Jung et al. |
| 2008/0033434 A1 | 2/2008 | Boomer |

(56) References Cited

U.S. PATENT DOCUMENTS

| | | |
|---|---|---|
| 2008/0033436 A1 | 2/2008 | Gordon |
| 2008/0048855 A1 | 2/2008 | Berger |
| 2008/0051784 A1 | 2/2008 | Gollogly |
| 2008/0082118 A1 | 4/2008 | Edidin et al. |
| 2008/0086128 A1 | 4/2008 | Lewis |
| 2008/0097188 A1 | 4/2008 | Pool et al. |
| 2008/0097249 A1 | 4/2008 | Pool et al. |
| 2008/0097487 A1 | 4/2008 | Pool et al. |
| 2008/0097496 A1 | 4/2008 | Chang et al. |
| 2008/0108995 A1 | 5/2008 | Conway et al. |
| 2008/0161933 A1 | 7/2008 | Grotz et al. |
| 2008/0167685 A1 | 7/2008 | Allard et al. |
| 2008/0172063 A1 | 7/2008 | Taylor |
| 2008/0172072 A1 | 7/2008 | Pool et al. |
| 2008/0177319 A1 | 7/2008 | Schwab |
| 2008/0177326 A1 | 7/2008 | Thompson |
| 2008/0190237 A1 | 8/2008 | Radinger et al. |
| 2008/0228186 A1 | 9/2008 | Gall et al. |
| 2008/0255615 A1 | 10/2008 | Vittur et al. |
| 2008/0272928 A1 | 11/2008 | Shuster |
| 2008/0275557 A1 | 11/2008 | Makower et al. |
| 2008/0306538 A1 | 12/2008 | Moore |
| 2009/0030462 A1 | 1/2009 | Buttermann |
| 2009/0076597 A1 | 3/2009 | Dahlgren et al. |
| 2009/0082815 A1 | 3/2009 | Zylber et al. |
| 2009/0088766 A1 | 4/2009 | Magill |
| 2009/0088803 A1 | 4/2009 | Justis et al. |
| 2009/0093820 A1 | 4/2009 | Trieu et al. |
| 2009/0093890 A1 | 4/2009 | Gelbart |
| 2009/0112263 A1 | 4/2009 | Pool et al. |
| 2009/0118733 A1 | 5/2009 | Orsak |
| 2009/0163780 A1 | 6/2009 | Tieu |
| 2009/0171356 A1 | 7/2009 | Klett |
| 2009/0192514 A1 | 7/2009 | Feinberg et al. |
| 2009/0198144 A1 | 8/2009 | Phillips et al. |
| 2009/0204154 A1 | 8/2009 | Kiester |
| 2009/0204156 A1 | 8/2009 | McClintock |
| 2009/0216113 A1 | 8/2009 | Meier et al. |
| 2009/0275984 A1 | 11/2009 | Kim et al. |
| 2010/0004654 A1 | 1/2010 | Schmitz et al. |
| 2010/0009430 A1 | 1/2010 | Wan et al. |
| 2010/0057127 A1 | 3/2010 | McGuire et al. |
| 2010/0094302 A1* | 4/2010 | Pool ............... A61B 17/7079 606/90 |
| 2010/0094303 A1 | 4/2010 | Chang |
| 2010/0094304 A1 | 4/2010 | Pool |
| 2010/0094306 A1 | 4/2010 | Chang et al. |
| 2010/0100185 A1 | 4/2010 | Trieu et al. |
| 2010/0106192 A1 | 4/2010 | Barry |
| 2010/0114322 A1 | 5/2010 | Clifford et al. |
| 2010/0121323 A1 | 5/2010 | Pool et al. |
| 2010/0130941 A1 | 5/2010 | Conlon et al. |
| 2010/0137872 A1 | 6/2010 | Kam et al. |
| 2010/0145449 A1 | 6/2010 | Makower et al. |
| 2010/0145462 A1 | 6/2010 | Ainsworth et al. |
| 2010/0168751 A1 | 7/2010 | Anderson et al. |
| 2010/0217271 A1 | 8/2010 | Pool |
| 2010/0249782 A1 | 9/2010 | Durham |
| 2010/0249847 A1 | 9/2010 | Jung |
| 2010/0256626 A1 | 10/2010 | Muller et al. |
| 2010/0262239 A1 | 10/2010 | Boyden et al. |
| 2010/0280551 A1 | 11/2010 | Pool |
| 2010/0318129 A1 | 12/2010 | Seme et al. |
| 2010/0331883 A1 | 12/2010 | Schmitz et al. |
| 2011/0004076 A1 | 1/2011 | Janna et al. |
| 2011/0057756 A1 | 3/2011 | Marinescu et al. |
| 2011/0060336 A1 | 3/2011 | Pool |
| 2011/0066188 A1 | 3/2011 | Seme et al. |
| 2011/0098748 A1 | 4/2011 | Jangra |
| 2011/0152725 A1 | 6/2011 | Demir et al. |
| 2011/0196435 A1 | 8/2011 | Forsell |
| 2011/0202138 A1 | 8/2011 | Shenoy et al. |
| 2011/0218534 A1 | 9/2011 | Prandi |
| 2011/0237861 A1 | 9/2011 | Pool |
| 2011/0238126 A1 | 9/2011 | Soubeiran |
| 2011/0245878 A1 | 10/2011 | Franks |
| 2011/0257655 A1 | 10/2011 | Copf, Jr. |
| 2011/0284014 A1 | 11/2011 | Cadeddu et al. |
| 2012/0004494 A1 | 1/2012 | Payne |
| 2012/0019341 A1 | 1/2012 | Gabay et al. |
| 2012/0019342 A1 | 1/2012 | Gabay et al. |
| 2012/0035656 A1 | 2/2012 | Pool |
| 2012/0035661 A1 | 2/2012 | Pool |
| 2012/0053633 A1 | 3/2012 | Stauch |
| 2012/0088953 A1 | 4/2012 | King |
| 2012/0109207 A1 | 5/2012 | Trieu |
| 2012/0116535 A1 | 5/2012 | Ratron et al. |
| 2012/0130428 A1* | 5/2012 | Hunziker ........... A61B 17/7016 606/258 |
| 2012/0150230 A1 | 6/2012 | Felix |
| 2012/0157996 A1 | 6/2012 | Walker |
| 2012/0158061 A1 | 6/2012 | Koch et al. |
| 2012/0172883 A1 | 7/2012 | Sayago |
| 2012/0179215 A1 | 7/2012 | Soubeiran |
| 2012/0203282 A1 | 8/2012 | Sachs |
| 2012/0209265 A1 | 8/2012 | Pool |
| 2012/0209269 A1 | 8/2012 | Pool |
| 2012/0221106 A1 | 8/2012 | Makower et al. |
| 2012/0271353 A1 | 10/2012 | Barry |
| 2012/0283781 A1 | 11/2012 | Arnin |
| 2012/0296234 A1 | 11/2012 | Wilhelm et al. |
| 2012/0329882 A1 | 12/2012 | Messersmith et al. |
| 2013/0013066 A1 | 1/2013 | Landry et al. |
| 2013/0072932 A1 | 3/2013 | Stauch |
| 2013/0123847 A1 | 5/2013 | Anderson et al. |
| 2013/0138017 A1 | 5/2013 | Jundt et al. |
| 2013/0138154 A1 | 5/2013 | Reiley |
| 2013/0150863 A1 | 6/2013 | Baumgartner |
| 2013/0150889 A1 | 6/2013 | Fening et al. |
| 2013/0165976 A1 | 6/2013 | Gunn |
| 2013/0178903 A1 | 7/2013 | Abdou |
| 2013/0211521 A1 | 8/2013 | Shenoy et al. |
| 2013/0245692 A1 | 9/2013 | Hayes et al. |
| 2013/0253344 A1 | 9/2013 | Griswold et al. |
| 2013/0253587 A1 | 9/2013 | Carls et al. |
| 2013/0261672 A1 | 10/2013 | Horvath |
| 2013/0296863 A1 | 11/2013 | Globerman et al. |
| 2013/0296864 A1 | 11/2013 | Burley et al. |
| 2013/0296940 A1 | 11/2013 | Northcutt et al. |
| 2013/0325006 A1 | 12/2013 | Michelinie et al. |
| 2013/0325071 A1 | 12/2013 | Niemiec et al. |
| 2014/0005788 A1 | 1/2014 | Haaja |
| 2014/0025172 A1 | 1/2014 | Lucas et al. |
| 2014/0052134 A1 | 2/2014 | Orisek |
| 2014/0058392 A1 | 2/2014 | Mueckter et al. |
| 2014/0058450 A1 | 2/2014 | Arlet |
| 2014/0066987 A1 | 3/2014 | Hestad et al. |
| 2014/0088715 A1 | 3/2014 | Ciupik |
| 2014/0128920 A1 | 5/2014 | Kantelhardt |
| 2014/0142631 A1 | 5/2014 | Hunziker |
| 2014/0163664 A1 | 6/2014 | Goldsmith |
| 2014/0236234 A1 | 8/2014 | Kroll et al. |
| 2014/0236311 A1 | 8/2014 | Vicatos et al. |
| 2014/0257412 A1 | 9/2014 | Patty et al. |
| 2014/0277446 A1 | 9/2014 | Clifford et al. |
| 2014/0296918 A1 | 10/2014 | Fening et al. |
| 2014/0303538 A1 | 10/2014 | Baym et al. |
| 2014/0303539 A1 | 10/2014 | Baym et al. |
| 2014/0324047 A1 | 10/2014 | Zahrly |
| 2014/0358150 A1 | 12/2014 | Kaufman et al. |
| 2015/0105782 A1 | 4/2015 | D'Lima et al. |
| 2015/0105824 A1 | 4/2015 | Moskowitz et al. |

FOREIGN PATENT DOCUMENTS

| | | |
|---|---|---|
| CN | 101040807 A | 9/2007 |
| DE | 1541262 A1 | 6/1969 |
| DE | 8515687 U1 | 12/1985 |
| DE | 19626230 A1 | 1/1998 |
| DE | 19745654 A1 | 4/1999 |
| DE | 102005045070 A1 | 4/2007 |
| EP | 0663184 A1 | 7/1995 |
| EP | 1905388 A1 | 4/2008 |
| FR | 2901991 A1 | 12/2007 |

(56) References Cited

FOREIGN PATENT DOCUMENTS

| FR | 2900563 | B1 | 8/2008 |
|---|---|---|---|
| FR | 2892617 | B1 | 9/2008 |
| FR | 2916622 | B1 | 9/2009 |
| FR | 2961386 | B1 | 7/2012 |
| JP | H0956736 | | 3/1997 |
| JP | 2002500063 | A | 1/2002 |
| WO | 9844858 | A1 | 10/1998 |
| WO | 0124697 | A1 | 4/2001 |
| WO | 0145485 | A3 | 6/2001 |
| WO | 0145487 | A2 | 6/2001 |
| WO | 0167973 | A2 | 9/2001 |
| WO | 0178614 | A1 | 10/2001 |
| WO | 2006090380 | A2 | 8/2006 |
| WO | 2007013059 | A3 | 2/2007 |
| WO | 2007025191 | A1 | 3/2007 |
| WO | 2007118179 | A2 | 10/2007 |
| WO | 2007144489 | A2 | 12/2007 |
| WO | 2008003952 | A1 | 1/2008 |
| WO | WO2007015239 | A3 | 1/2008 |
| WO | 2008040880 | A2 | 4/2008 |
| WO | 2011116158 | A3 | 9/2011 |
| WO | 2013119528 | A1 | 8/2013 |
| WO | 2014040013 | A1 | 3/2014 |

OTHER PUBLICATIONS

Ahlbom et al., "Guidelines for limiting exposure to time-varying electric, magnetic, and electromagnetic fields (up to 300 GHz). International Commission on Non-Ionizing Radiation Protection.", Health Physics, 1998, pp. 494-522, 74, No. 4.
Amer et al., "Evaluation of treatment of late-onset tibia vara using gradual angulation translation high tibial osteotomy", ACTA Orthopaedica Belgica, 2010, pp. 360-366, 76, No. 3.
Angrisani et al., "Lap-Band® Rapid Port™ System: Preliminary results in 21 patients", Obesity Surgery, 2005, p. 936, 15, No. 7.
Baumgart et al., "A fully implantable, programmable distraction nail (Fitbone)—new perspectives for corrective and reconstructive limb surgery.", Practice of Intramedullary Locked Nails, 2006, pp. 189-198.
Baumgart et al., "The bioexpandable prosthesis: A new perspective after resection of malignant bone tumors in children.", J Pediatr Hematol Oncol, 2005, pp. 452-455, 27, No. 8.
Bodó et al., "Development of a tension-adjustable implant for anterior cruciate ligament reconstruction.", Eklem Hastaliklari ve Cerrahisi—Joint Diseases and Related Surgery, 2008, pp. 27-32, 19, No. 1.
Boudjemline et al., "Off-label use of an adjustable gastric banding system for pulmonary artery banding.", The Journal of Thoracic and Cardiovascular Surgery, 2006, pp. 1130-1135, 131, No. 5.
Brown et al., "Single port surgery and the Dundee Endocone.", SAGES Annual Scientific Sessions: Emerging Technology Poster Abstracts, 2007, ETP007, pp. 323-324.
Buchowski et al., "Temporary internal distraction as an aid to correction of severe scoliosis", J Bone Joint Surg Am, 2006, pp. 2035-2041, 88-A, No. 9.
Burghardt et al., "Mechanical failure of the Intramedullary Skeletal Kinetic Distractor in limb lengthening.", J Bone Joint Surg Br, 2011, pp. 639-643, 93-B, No. 5.
Burke, "Design of a minimally invasive non fusion device for the surgical management of scoliosis in the skeletally immature", Studies in Health Technology and Informatics, 2006, pp. 378-384, 123.
Carter et al., "A cumulative damage model for bone fracture.", Journal of Orthopaedic Research, 1985, pp. 84-90, 3, No. 1.
Chapman et al., "Laparoscopic adjustable gastric banding in the treatment of obesity: A systematic literature review.", Surgery, 2004, pp. 326-351, 135, No. 3.
Cole et al., "Operative technique intramedullary skeletal kinetic distractor: Tibial surgical technique.", Orthofix, 2005.

Cole et al., "The intramedullary skeletal kinetic distractor (ISKD): first clinical results of a new intramedullary nail for lengthening of the femur and tibia.", Injury, 2001, pp. S-D-129-S-D-139, 32.
Dailey et al., "A novel intramedullary nail for micromotion stimulation of tibial fractures.", Clinical Biomechanics, 2012, pp. 182-188, 27, No. 2.
Daniels et al., "A new method for continuous intraoperative measurement of Harrington rod loading patterns.", Annals of Biomedical Engineering, 1984, pp. 233-246, 12, No. 3.
De Giorgi et al., "Cotrel-Dubousset instrumentation for the treatment of severe scoliosis.", European Spine Journal, 1999, pp. 8-15, No. 1.
Dorsey et al., "The stability of three commercially available implants used in medial opening wedge high tibial osteotomy.", Journal of Knee Surgery, 2006, pp. 95-98, 19, No. 2.
Edeland et al., "Instrumentation for distraction by limited surgery in scoliosis treatment.", Journal of Biomedical Engineering, 1981, pp. 143-146, 3, No. 2.
Elsebaie, "Single growing rods (Review of 21 cases). Changing the foundations: Does it affect the results?", Journal of Child Orthop, 2007, 1:258.
Ember et al., "Distraction forces required during growth rod lengthening.", J of Bone Joint Surg BR, 2006, p. 229, 88-B, No. Suppl. II.
European Patent Office, "Observations by a third party under Article 115 EPC in EP08805612 by Soubeiran.", 2010.
Fabry et al., "A technique for prevention of port complications after laparoscopic adjustable silicone gastric banding.", Obesity Surgery, 2002, pp. 285-288, 12, No. 2.
Fried et al., "In vivo measurements of different gastric band pressures towards the gastric wall at the stoma region.", Obesity Surgery, 2004, p. 914, 14, No. 7.
Gao et al., CHD7 gene polymorphisms are associated with susceptibility to idiopathic scoliosis, American Journal of Human Genetics, 2007, pp. 957-965, 80.
Gebhart et al., "Early clinical experience with a custom made growing endoprosthesis in children with malignant bone tumors of the lower extremity actioned by an external permanent magnet; The Phenix M. system", International Society of Limb Salvage 14th International Symposium on Limb Salvage. Sep. 3, 2007, Hamburg, Germany. (2 pages).
Gillespie et al. "Harrington instrumentation without fusion.", J Bone Joint Surg Br, 1981, p. 461, 63-B, No. 3.
Goodship et al., "Strain rate and timing of stimulation in mechanical modulation of fracture healing.", Clinical Orthopaedics and Related Research, 1998, pp. S105-S115, No. 355S.
Grass et al., "Intermittent distracting rod for correction of high neurologic risk congenital scoliosis.", SPINE, 1997, pp. 1922-1927, 22, No. 16.
Gray, "Gray's anatomy of the human body.", http://education.yahoo.com/reference/gray/subjects/subject/128, published Jul. 1, 2007.
Grimer et al. "Non-invasive extendable endoprostheses for children—Expensive but worth it!", International Society of Limb Salvage 14th International Symposium on Limb Salvage, 2007.
Grünert, "The development of a totally implantable electronic sphincter." (translated from the German "Die Entwicklung eines total implantierbaren elektronischen Sphincters"), Langenbecks Archiv fur Chirurgie, 1969, pp. 1170-1174, 325.
Guichet et al. "Gradual femoral lengthening with the Albizzia intramedullary nail", J Bone Joint Surg Am, 2003, pp. 838-848, 85-A, No. 5.
Gupta et al., "Non-invasive distal femoral expandable endoprosthesis for limb-salvage surgery in paediatric tumours.", J Bone Joint Surg Br, 2006, pp. 649-654, 88-B, No. 5.
Hankemeier et al., "Limb lengthening with the Intramedullary Skeletal Kinetic Distractor (ISKD).", Oper Orthop Traumatol, 2005, pp. 79-101, 17, No. 1.
Harrington, "Treatment of scoliosis. Correction and internal fixation by spine instrumentation.", J Bone Joint Surg Am, 1962, pp. 591-610, 44-A, No. 4.
Hennig et al., "The safety and efficacy of a new adjustable plate used for proximal tibial opening wedge osteotomy in the treatment of unicompartmental knee osteoarthrosis.", Journal of Knee Surgery, 2007, pp. 6-14, 20, No. 1.

(56) References Cited

OTHER PUBLICATIONS

Hofmeister et al., "Callus distraction with the Albizzia nail.", Practice of Intramedullary Locked Nails, 2006, pp. 211-215.
Horbach et al., "First experiences with the routine use of the Rapid Port™ system with the Lap-Band®.", Obesity Surgery, 2006, p. 418, 16, No. 4.
Hyodo et al., "Bone transport using intramedullary fixation and a single flexible traction cable.", Clinical Orthopaedics and Related Research, 1996, pp. 256-268, 325.
International Commission on Non-Ionizing Radiation Protection, "Guidelines on limits of exposure to static magnetic fields." Health Physics, 2009, pp. 504-514, 96, No. 4.
INVIS®/Lamello Catalog, 2006, Article No. 68906A001 GB.
Kasliwal et al., "Management of high-grade spondylolisthesis.", Neurosurgery Clinics of North America, 2013, pp. 275-291, 24, No. 2.
Kenawey et al., "Leg lengthening using intramedullay skeletal kinetic distractor: Results of 57 consecutive applications.", Injury, 2011, pp. 150-155, 42, No. 2.
Kent et al., "Assessment and correction of femoral malrotation following intramedullary nailing of the femur.", Acta Orthop Belg, 2010, pp. 580-584, 76, No. 5.
Klemme et al., "Spinal instrumentation without fusion for progressive scoliosis in young children", Journal of Pediatric Orthopaedics. 1997, pp. 734-742, 17, No. 6.
Korenkov et al., "Port function after laparoscopic adjustable gastric banding for morbid obesity.", Surgical Endoscopy, 2003, pp. 1068-1071, 17, No. 7.
Krieg et al., "Leg lengthening with a motorized nail in adolescents.", Clinical Orthopaedics and Related Research, 2008, pp. 189-197, 466, No. 1.
Kucukkaya et al., "The new intramedullary cable bone transport technique.", Journal of Orthopaedic Trauma, 2009, pp. 531-536, 23, No. 7.
Lechner et al., "In vivo band manometry: A new method in band adjustment", Obesity Surgery, 2005, p. 935, 15, No. 7.
Lechner et al., "Intra-band manometry for band adjustments: The basics", Obesity Surgery, 2006, pp. 417-418, 16, No. 4.
Li et al., "Bone transport over an intramedullary nail: A case report with histologic examination of the regenerated segment.", Injury, 1999, pp. 525-534, 30, No. 8.
Lonner, "Emerging minimally invasive technologies for the management of scoliosis.", Orthopedic Clinics of North America, 2007, pp. 431-440, 38, No. 3.
Matthews et al., "Magnetically adjustable intraocular lens.", Journal of Cataract and Refractive Surgery, 2003, pp. 2211-2216, 29, No. 11.
MicroMotion, "Micro Drive Engineering. General catalogue.", 2009, pp. 14-24.
Mineiro et al., "Subcutaneous rodding for progressive spinal curvatures: Early results.", Journal of Pediatric Orthopaedics, 2002, pp. 290-295, 22, No. 3.
Moe et al., "Harrington instrumentation without fusion plus external orthotic support for the treatment of difficult curvature problems in young children.", Clinical Orthopaedics and Related Research, 1984, pp. 35-45, 185.
Montague et al., "Magnetic gear dynamics for servo control.", Melecon 2010—2010 15th IEEE Mediterranean Electrotechnical Conference, Valletta, 2010, pp. 1192-1197.
Montague et al., "Servo control of magnetic gears.", IEEE/ASME Transactions on Mechatronics, 2012, pp. 269-278, 17, No. 2.
Nachemson et al., "Intravital wireless telemetry of axial forces in Harrington distraction rods in patients with idiopathic scoliosis.", The Journal of Bone and Joint Surgery, 1971, pp. 445-465, 53, No. 3.
Nachlas et al., "The cure of experimental scoliosis by directed growth control.", The Journal of Bone and Joint Surgery, 1951, pp. 24-34, 33-A, No. 1.
Newton et al., "Fusionless scoliosis correction by anterolateral tethering . . . can it work?. ", 39th Annual Scoliosis Research Society Meeting, 2004.
Oh et al., "Bone transport over an intramedullary nail for reconstruction of long bone defects in tibia.", Archives of Orthopaedic and Trauma Surgery, 2008, pp. 801-808, 128, No. 8.
Ozcivici et al., "Mechanical signals as anabolic agents in bone.", Nature Reviews Rheumatology, 2010, pp. 50-59, 6, No. 1.
Piorkowski et al., Preventing Port Site Inversion in Laparoscopic Adjustable Gastric Banding, Surgery for Obesity and Related Diseases, 2007, 3(2), pp. 159-162, Elsevier; New York, U.S.A.
Prontes, "Longest bone in body.", eHow.com, 2012.
Rathjen et al., "Clinical and radiographic results after implant removal in idiopathic scoliosis.", SPINE, 2007, pp. 2184-2188, 32, No. 20.
Ren et al., "Laparoscopic adjustable gastric banding: Surgical technique", Journal of Laparoendoscopic & Advanced Surgical Techniques, 2003, pp. 257-263, 13, No. 4.
Reyes-Sanchez et al., "External fixation for dynamic correction of severe scoliosis", The Spine Journal, 2005, pp. 418-426, 5, No. 4.
Rinsky et al., "Segmental instrumentation without fusion in children with progressive scoliosis.", Journal of Pediatric Orthopedics, 1985, pp. 687-690, 5, No. 6.
Rode et al., "A simple way to adjust bands under radiologic control", Obesity Surgery, 2006, p. 418, 16, No. 4.
Schmerling et al., "Using the shape recovery of nitinol in the Harrington rod treatment of scoliosis.", Journal of Biomedical Materials Research, 1976, pp. 879-892, 10, No. 6.
Scott et al., "Transgastric, transcolonic and transvaginal cholecystectomy using magnetically anchored instruments.", SAGES Annual Scientific Sessions, Poster Abstracts, Apr. 18-22, 2007, P511, p. 306.
Sharke, "The machinery of life", Mechanical Engineering Magazine, Feb. 2004, Printed from Internet site Oct. 24, 2007 http://www.memagazine.org/contents/current/features/moflife/moflife.html.
Shiha et al., "Ilizarov gradual correction of genu varum deformity in adults.", Acta Orthop Belg, 2009, pp. 784-791, 75, No. 6.
Simpson et al., "Femoral lengthening with the intramedullary skeletal kinetic distractor.", Journal of Bone and Joint Surgery, 2009, pp. 955-961, 91-B, No. 7.
Smith, "The use of growth-sparing instrumentation in pediatric spinal deformity.", Orthopedic Clinics of North America, 2007, pp. 547-552, 38, No. 4.
Soubeiran et al. "The Phenix M System, a fully implanted non-invasive lengthening device externally controllable through the skin with a palm size permanent magnet. Applications in limb salvage." International Society of Limb Salvage 14th International Symposium on Limb Salvage, Sep. 13, 2007, Hamburg, Germany. (2 pages).
Soubeiran et al., "The Phenix M System. A fully implanted lengthening device externally controllable through the skin with a palm size permanent magnet; Applications to pediatric orthopaedics", 6th European Research Conference in Pediatric Orthopaedics, Oct. 6, 2006, Toulouse, France (7 pages).
Stokes et al., "Reducing radiation exposure in early-onset scoliosis surgery patients: Novel use of ultrasonography to measure lengthening in magnetically-controlled growing rods. Prospective validation study and assessment of clinical algorithm", 20th International Meeting on Advanced Spine Techniques, Jul. 11, 2013. Vancouver, Canada. Scoliosis Research Society.
Sun et al., "Masticatory mechanics of a mandibular distraction osteogenesis site: Interfragmentary micromovement.", Bone, 2007, pp. 188-196, 41, No. 2.
Synthes Spine, "VEPTR II. Vertical Expandable Prosthetic Titanium Rib II: Technique Guide.", 2008, 40 pgs.
Synthes Spine, "VEPTR Vertical Expandable Prosthetic Titanium Rib, Patient Guide.", 2005, 26 pgs.
Takaso et al., "New remote-controlled growing-rod spinal instrumentation possibly applicable for scoliosis in young children.", Journal of Orthopaedic Science, 1998, pp. 336-340, 3, No. 6.
Teli et al., "Measurement of forces generated during distraction of growing rods.", Journal of Children's Orthopaedics, 2007, pp. 257-258, 1, No. 4.

(56) References Cited

OTHER PUBLICATIONS

Tello, "Harrington instrumentation without arthrodesis and consecutive distraction program for young children with severe spinal deformities: Experience and technical details.", The Orthopedic Clinics of North America, 1994, pp. 333-351, 25, No. 2.

Thaller et al., "Limb lengthening with fully implantable magnetically actuated mechanical nails (PHENIX®)—Preliminary results.", Injury, 2014 (E-published Oct. 28, 2013), pp. S60-S65, 45.

Thompson et al., "Early onset scoliosis: Future directions", 2007, J Bone Joint Surg Am, pp. 163-166, 89-A, Suppl 1.

Thompson et al., "Growing rod techniques in early-onset scoliosis", Journal of Pediatric Orthopedics, 2007, pp. 354-361, 27, No. 3.

Thonse et al., "Limb lengthening with a fully implantable, telescopic, intramedullary nail.", Operative Techniques in Orthopedics, 2005, pp. 355-362, 15, No. 4.

Trias et al., "Dynamic loads experienced in correction of idiopathic scoliosis using two types of Harrington rods.", SPINE, 1979, pp. 228-235, 4, No. 3.

Verkerke et al., "An extendable modular endoprosthetic system for bone tumor management in the leg", Journal of Biomedical Engineering, 1990, pp. 91-96, 12, No. 2.

Verkerke et al., "Design of a lengthening element for a modular femur endoprosthetic system", Proceedings of the Institution of Mechanical Engineers Part H: Journal of Engineering in Medicine, 1989, pp. 97-102, 203, No. 2.

Verkerke et al., "Development and test of an extendable endoprosthesis for bone reconstruction in the leg.", The International Journal of Artificial Organs, 1994, pp. 155-162, 17, No. 3.

Weiner et al., "Initial clinical experience with telemetrically adjustable gastric banding", Surgical Technology International, 2005, pp. 63-69, 15.

Wenger, "Spine jack operation in the correction of scoliotic deformity: A direct intrathoracic attack to straighten the laterally bent spine: Preliminary report", Arch Surg, 1961, pp. 123-132 (901-910), 83, No. 6.

White, III et al., "The clinical biomechanics of scoliosis.", Clinical Orthopaedics and Related Research, 1976, pp. 100-112, 118.

Yonnet, "A new type of permanent magnet coupling.", IEEE Transactions on Magnetics, 1981, pp. 2991-2993, 17, No. 6.

Yonnet, "Passive magnetic bearings with permanent magnets.", IEEE Transactions on Magnetics, 1978, pp. 803-805, 14, No. 5.

Zheng et al., "Force and torque characteristics for magnetically driven blood pump.", Journal of Magnetism and Magnetic Materials, 2002, pp. 292-302, 241, No. 2.

\* cited by examiner

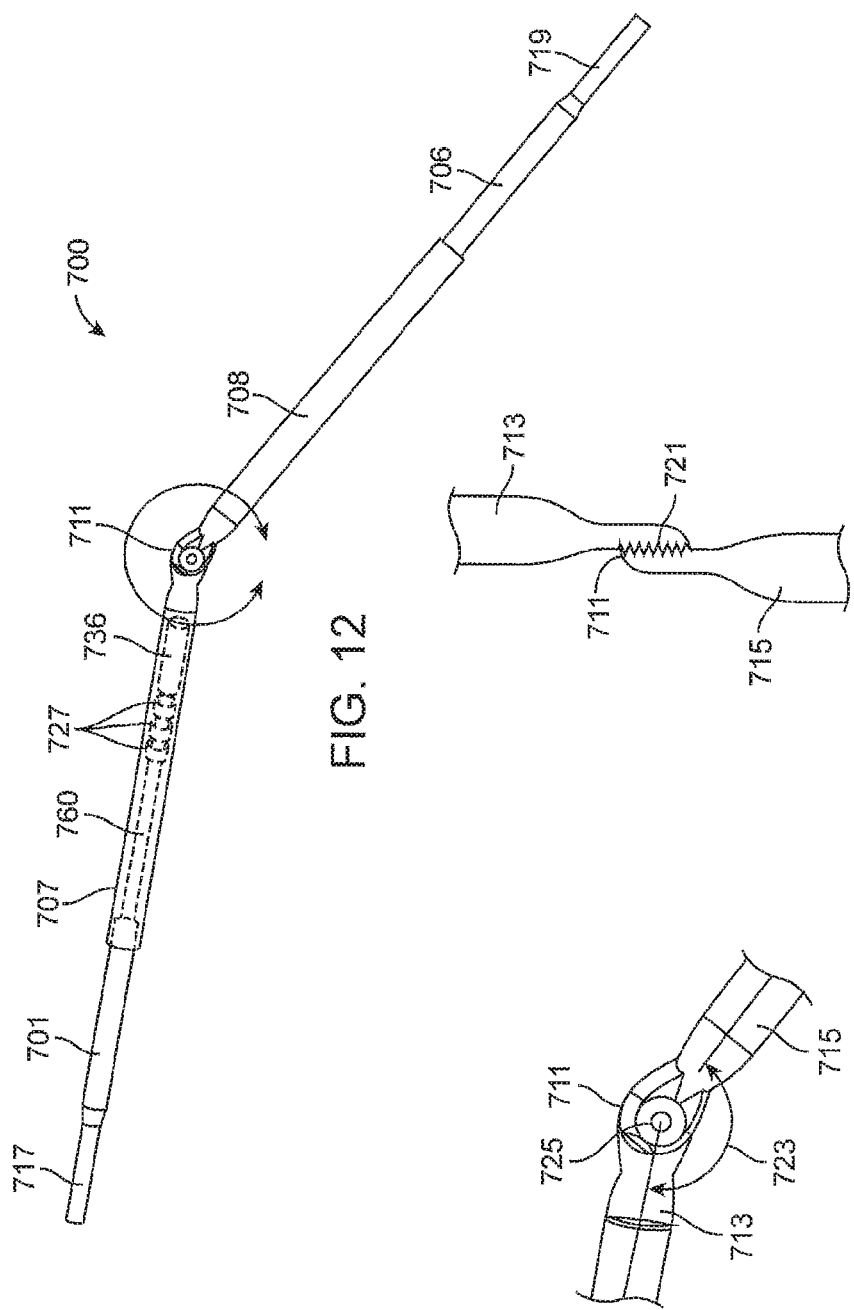

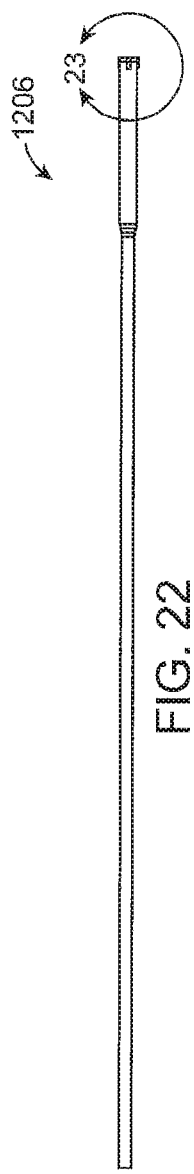
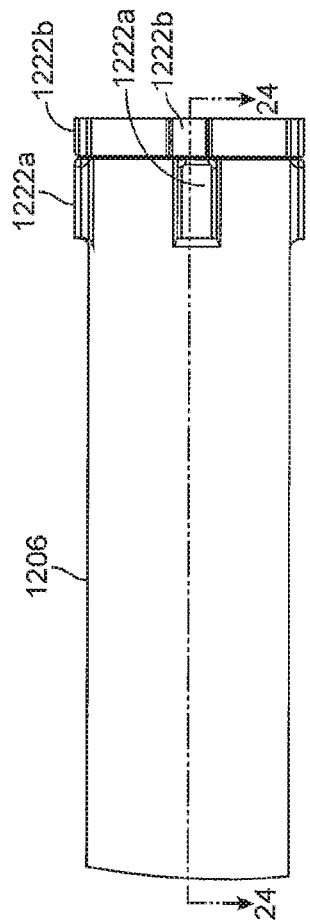
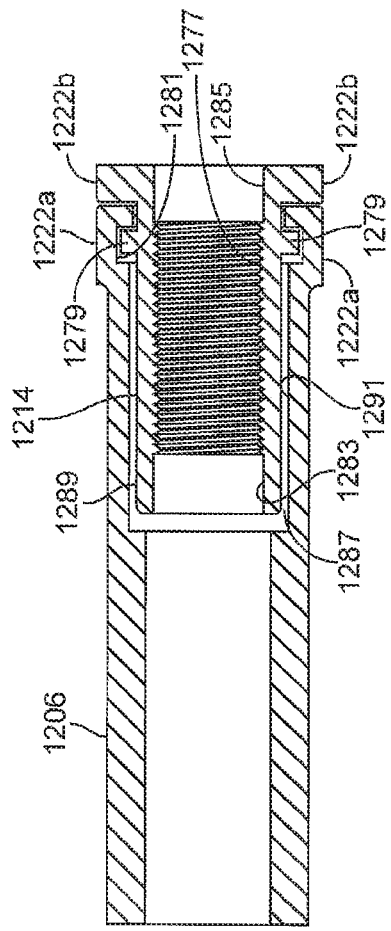

MAGNETIC IMPLANTS WITH IMPROVED ANATOMICAL COMPATIBILITY

CROSS REFERENCE TO RELATED APPLICATIONS

This application is a continuation of U.S. application Ser. No. 13/525,058, filed on Jun. 15, 2012, now abandoned, the content of which is hereby incorporated by reference in its entirety.

FIELD OF THE INVENTION

The field of the invention generally relates to medical devices for treating disorders of the skeletal system.

BACKGROUND

Scoliosis is a general term for the sideways (lateral) curving of the spine, usually in the thoracic or thoracolumbar region. Often, there is also a rotation of the spine as well as curvature. Scoliosis is commonly broken up into different treatment groups, Adolescent Idiopathic Scoliosis, Early Onset Scoliosis and Adult Scoliosis.

Adolescent Idiopathic Scoliosis (AIS) typically affects children between ages 10 and 16, and becomes most severe during growth spurts that occur as the body is developing. One to two percent of children between ages 10 and 16 have some amount of scoliosis. Of every 1000 children, two to five develop curves that are serious enough to require treatment. The degree of scoliosis is typically described by the Cobb angle, which is determined, usually from x-ray images, by taking the most tilted vertebrae above and below the apex of the curved portion and measuring the angle between intersecting lines drawn perpendicular to the top of the top vertebrae and the bottom of the bottom. The term idiopathic refers to the fact that the exact cause of this curvature is unknown. Some have speculated that scoliosis occurs when, during rapid growth phases, the ligamentum flavum of the spine is too tight and hinders symmetric growth of the spine. For example, as the anterior portion of the spine elongates faster than the posterior portion, the thoracic spine begins to straighten, until it curves laterally, often with an accompanying rotation. In more severe cases, this rotation actually creates a noticeable deformity, wherein one shoulder is lower than the other. Currently, many school districts perform external visual assessment of spines, for example in all fifth grade students. For those students in whom an "S" shape or "C" shape is identified, instead of an "I" shape, a recommendation is given to have the spine examined by a physician, and commonly followed-up with periodic spinal x-rays.

Typically, patients with a Cobb angle of 20° or less are not treated, but are continually followed up, often with subsequent x-rays. Patients with a Cobb angle of 40° or greater are usually recommended for fusion surgery. It should be noted that many patients do not receive this spinal assessment, for numerous reasons. Many school districts do not perform this assessment, and many children do not regularly visit a physician, so often, the curve progresses rapidly and severely. In AIS, the ratio of females to males for curves under 10° is about one to one, however, at angles above 30°, females outnumber males by as much as eight to one. Fusion surgery can be performed on the AIS patients or on adult scoliosis patients. In a typical posterior fusion surgery, an incision is made down the length of the back and Titanium or stainless steel straightening rods are placed along the curved portion. These rods are typically secured to the vertebral bodies, for example with bone screws, or more specifically pedicle screws, in a manner that allows the spine to be straightened. Usually, at the section desired for fusion, the intervertebral disks are removed and bone graft material is placed to create the fusion. If this is autologous material, the bone is harvested from a hip via a separate incision.

Alternatively, the fusion surgery may be performed anteriorly. A lateral and anterior incision is made for access. Usually, one of the lungs is deflated in order to allow access to the spine from this anterior approach. In a less-invasive version of the anterior procedure, instead of the single long incision, approximately five incisions, each about three to four cm long are made in several of the intercostal spaces (between the ribs) on one side of the patient. In one version of this minimally invasive surgery, tethers and bone screws are placed and are secured to the vertebra on the anterior convex portion of the curve. Currently, clinical trials are being performed which use staples in place of the tether/screw combination. One advantage of this surgery in comparison with the posterior approach is that the scars from the incisions are not as dramatic, though they are still located in a visible area, when a bathing suit, for example, is worn. The staples have had some difficulty in the clinical trials. The staples tend to pull out of the bone when a critical stress level is reached.

Commonly, after surgery, the patient will wear a brace for a few months as the fusing process occurs. Once the patient reaches spinal maturity, it is difficult to remove the rods and associated hardware in a subsequent surgery, because the fusion of the vertebra usually incorporates the rods themselves. Standard practice is to leave this implant in for life. With either of these two surgical methods, after fusion, the patient's spine is now straight, but depending on how many vertebra were fused, there are often limitations in the degree of flexibility, both in bending and twisting. As these fused patients mature, the fused section can impart large stresses on the adjacent non-fused vertebra, and often, other problems including pain can occur in these areas, sometimes necessitating further surgery. Many physicians are now interested in fusionless surgery for scoliosis, which may be able to eliminate some of the drawbacks of fusion.

One group of patients in which the spine is especially dynamic is the subset known as Early Onset Scoliosis (EOS), which typically occurs in children before the age of five. This is a more rare condition, occurring in only about one or two out of 10,000 children, but can be severe, sometimes affecting the normal development of organs. Because of the fact that the spines of these children will still grow a large amount after treatment, non-fusion distraction devices known as growing rods and a device known as the VEPTR—Vertical Expandable Prosthetic Titanium Rib ("Titanium Rib") have been developed. These devices are typically adjusted approximately every six months, to match the child's growth, until the child is at least eight years old, sometimes until they are 15 years old. Each adjustment requires a surgical incision to access the adjustable portion of the device. Because the patients may receive the device at an age as early as six months old, this treatment requires a large number of surgeries. Because of the multiple surgeries, these patients have a rather high preponderance of infection and other complications. A new magnetically controlled growing rod is now being used which allows adjustments to be done non-invasively, as reported in the article "Magnetically controlled growing rods for severe spinal curvature in young children: a prospective case series", Cheung et. al., Lancet, 2012.

Returning to the AIS patients, the treatment methodology for those with a Cobb angle between 20° and 40° is quite controversial. Many physicians prescribe a brace (for example, the Boston Brace), that the patient must wear on their body and under their clothes 18 to 23 hours a day until they become skeletally mature, for example to age 16. Because these patients are all passing through their socially demanding adolescent years, it is quite a serious prospect to be forced with the choice of either wearing a somewhat bulky brace that covers most of the upper body, having fusion surgery that may leave large scars and also limit motion, or doing nothing and running the risk of becoming disfigured and possibly disabled. It is commonly known that many patients have at times hidden their braces, for example, in a bush outside of school, in order to escape any related embarrassment. The patient compliance with brace wearing has been so problematic, that there have been special braces constructed which sense the body of the patient, and keep track of the amount of time per day that the brace is worn. Patients have even been known to place objects into unworn braces of this type in order to fool the sensor. Coupled with the inconsistent patient compliance with brace usage, is a feeling by many physicians that braces, even if used properly, are not at all effective at curing scoliosis. These physicians may agree that bracing can possibly slow down or even temporarily stop curve (Cobb angle) progression, but they have noted that as soon as the treatment period ends and the brace is no longer worn, often the scoliosis rapidly progresses, to a Cobb angle even more severe than it was at the beginning of treatment. Some say the reason for the supposed ineffectiveness of the brace is that it works only on a portion of the torso, and not on the entire spine. Currently a 500 patient clinical trial known as BrAIST (Bracing in Adolescent Idiopathic Scoliosis Trial) is enrolling patients, 50% of whom will be treated with the brace and 50% of who will simply be watched. The Cobb angle data will be measured continually up until skeletal maturity, or until a Cobb angle of 50° is reached, at which time the patient will likely undergo surgery.

Though this trial began as a randomized trial, it has since been changed to a "preference" trial, wherein the patients choose which treatment arm they will be in. This is partially because so many patients were rejecting the brace. Many physicians feel that the BrAIST trial will show that braces are completely ineffective. If this is the case, the quandary about what to do with AIS patients who have a Cobb angle of between 20° and 40° will only become more pronounced. It should be noted that the "20°. to 40°" patient population is as much as ten times larger than the "40° and greater" patient population. Currently, genetic scientists have found and continue to find multiple genes that may predispose scoliosis. Though gene tests have been developed, including a scoliosis score for risk of curve progression, some are still skeptical as to whether gene therapy would be possible to prevent scoliosis. However, the existence of a scoliosis gene would no doubt allow for easier and earlier identification of probable surgical patients.

Scoliosis is also present in patients with mature spines. One type of malady in mature patients is known as adult idiopathic scoliosis. It should be noted for reference purposes that the spine is actually mature in girls as young as fifteen or sixteen years old. In boys the maturity often occurs at a slightly older age of about eighteen years. Adult idiopathic scoliosis should be differentiated from what is known as de novo scoliosis or degenerative scoliosis, and which is predominantly caused by degeneration of the disc and facets with age, often combined with poor bone quality from osteopenia and osteoporosis. Oftentimes, fusion surgery in patients having mature spines with deformities requires significantly invasive measures to straighten the spine. This includes performing osteotomies (cutting out sections of the vertebrae) performed either from a posterior access or from an anterior access to the spine. Some types of osteotomies include Smith-Peterson osteotomy (SPO), pedicle subtraction osteotomy (PSO), and vertebral column resection (VCR). Because these osteotomies require more time and more invasive surgical techniques, their use adds significant cost and complications to fusion surgery.

There is a large population of mature spine patients with untreated scoliosis, in extreme cases with a Cobb angle as high as or greater than 60°, or even higher than 90°. In some cases, straightening this spine during a single fusion surgery could be problematic, even causing severe neurological problems. Many of these adults, though, do not have pain associated with this deformity while untreated, and live relatively normal lives, though oftentimes with restricted mobility and motion. It is contemplated that the devices and methods described herein also have application in the treatment of adult scoliosis. Adult scoliosis can continue to worsen with time. Though the adult is skeletally mature, the Cobb angle may still continue to increase with time. The relaxation or slight reduction in height that occurs in adults may have some relation with this increase in Cobb angle. Curves above 100° are rare, but they can be life-threatening if the spine twists the body to the point where pressure is put on the heart and lungs. The magnetically controlled growing rod has been described before as a treatment method of adult scoliosis, e.g., allowing adult scoliosis to be treated with a minimally invasive and/or fusionless approach. In addition, gradual adjustment of the spine may be desired, especially in the cases of very high Cobb angles. For example, it may be desired to limit the amount of stresses on the bones or on the implant materials, by first adjusting an adult scoliosis patient so that their Cobb angle is reduced 50% or less, then 15% or less each few months, until the spine is straight. As one example, the initial surgical implantation may reduce the Cobb angle by 50% or more by the physician performing manual distraction on the spine. Post-implantation, the Cobb angle can be reduced in a non-invasive manner by application of a constant or periodically changing distraction force. A first non-invasive adjustment may result in a Cobb angle reduction of less than 50%. Additional non-invasive adjustments may be performed which result in even smaller Cobb angle reductions (e.g., less than 15% from original Cobb angle).

In this regard, the Cobb angle may be reduced by a smaller amount over the next few months (e.g., less than around 15% each month post-operation). The non-invasive adjustment of a fusionless implant made possible by the invention allows for a gradual adjustment scheme of this nature. Moreover, the distraction forces used over this period of time are generally low (e.g., distraction force less than 45 pounds) which means, among other things, less patient discomfort, and less chance of failure within the adjustable rods. Non-invasive adjustments may be periodically performed when the patient visits his or her physician. This may occur over a span of more than one week (e.g., a several week process). Of course, the number and periodicity of the adjustments is a function of, among other things, the Cobb angle of the patient.

Oftentimes, the adult spine has less dense or even osteoporotic bone, so it may be desirable to combine the sort of gradual adjustment described here with additional methods to strengthen the bone, for example the bone of the vertebral bodies. One method is to strengthen the vertebral body by performing prophylactic vertebroplasty or kyphoplasty, wherein the internal area of the vertebral body is strengthened, for example by injection of bone cement or Polymethyl Methacrylate (PMMA). Additionally, if pedicle screws are used for fixation, the surface of the screws may be treated with a biologic material that promotes bone growth, or a surface characteristic that improves bone adhesion. Any of these methods would further improve the possibilities that the distraction forces would not cause fracture or other damage to the vertebrae of the patient.

In use, magnetically controlled growing rods are often cut and bent in the desired curves prior to implantation in the patient. It is common practice then to test the magnetically controlled growing rod immediately prior to placing in the patient (for example after cutting and bending) to confirm that it is completely operational. This often involves placing a sterile cover over the external adjustment device that is used to lengthen the magnetically controlled growing rod. This additional operation is not ideal because of the extra effort to bring the external adjustment device into the operating room, the extra effort to maintain sterility, and the fact that the external adjustment device contains powerful magnets, which can attract structures of the surgical table as well as surgical instruments.

SUMMARY

In one embodiment, a distraction system includes a first distraction device having a first adjustable portion and a first distraction rod configured to telescope within the first adjustable portion, the first adjustable portion having contained therein a first rotatable magnetic assembly mechanically coupled to a first screw configured to axially telescope the first distraction rod. The system includes a second distraction device having a second adjustable portion and a second distraction rod configured to telescope within the second adjustable portion, the second adjustable portion having contained therein a second rotatable magnetic assembly mechanically coupled to a second screw configured to axially telescope the second distraction rod. The distraction system includes an adjustable joint connecting one end of the first adjustable portion to one end of the second adjustable portion.

In another embodiment, a distraction system includes a first distraction device with a first adjustable portion having contained therein a first rotatable magnetic assembly. The system includes a second distraction device with a second adjustable portion having contained therein a second rotatable magnetic assembly; and a common distraction rod having first and second opposing ends, wherein a first end of the common distraction rod is mechanically coupled to the first rotatable magnetic assembly and wherein a second end of the common distraction rod is mechanically coupled to the second rotatable magnetic assembly.

In yet another embodiment, a distraction system includes an adjustable portion having contained therein a rotatable magnetic assembly, the adjustable portion being at least one of curved or angled; and a distraction rod mechanically coupled to the rotatable magnetic assembly via a screw and configured for telescopic movement relative to the adjustable portion.

In still another embodiment, a distraction system includes an adjustable portion having contained therein a rotatable magnetic assembly; a screw operatively coupled to the rotatable magnetic assembly; and a distraction rod having a recess formed therein, the recess containing a nut having internal threads, the nut having first and second collared ends disposed on either side of the internal threads, wherein the screw interfaces with the internal threads of the nut and wherein rotation of the rotatable magnetic assembly effectuates telescopic movement of the distraction rod relative to the adjustable portion.

In another embodiment, a distraction system includes an adjustable portion having contained therein a rotatable magnetic assembly; a distraction rod mechanically coupled to the rotatable magnetic assembly via a screw and configured for telescopic movement relative to the adjustable portion; and a distraction tester including a body having a cylindrical cavity passing through the body, wherein the distraction tester has a first circumferential portion of the body that has a higher mass of magnetically permeable material than a second circumferential portion, spaced apart from the first circumferential portion.

BRIEF DESCRIPTION OF THE DRAWINGS

FIG. 12 illustrates a distraction device having an angularly adjustable, lockable joint.

FIG. 13 illustrates a detailed view of the angularly adjustable, lockable joint of the distraction device of FIG. 12.

FIG. 14 illustrates a second detailed view of the angularly adjustable, lockable joint of the distraction device of FIG. 12.

FIG. 22 illustrates a distraction rod with an improved nut having collars.

FIG. 23 illustrates a detail of one end of the distraction rod of FIG. 22.

FIG. 24 illustrates a longitudinal section of FIG. 23 taken along lines 24-24.

DETAILED DESCRIPTION OF THE ILLUSTRATED EMBODIMENTS

Figure 1:
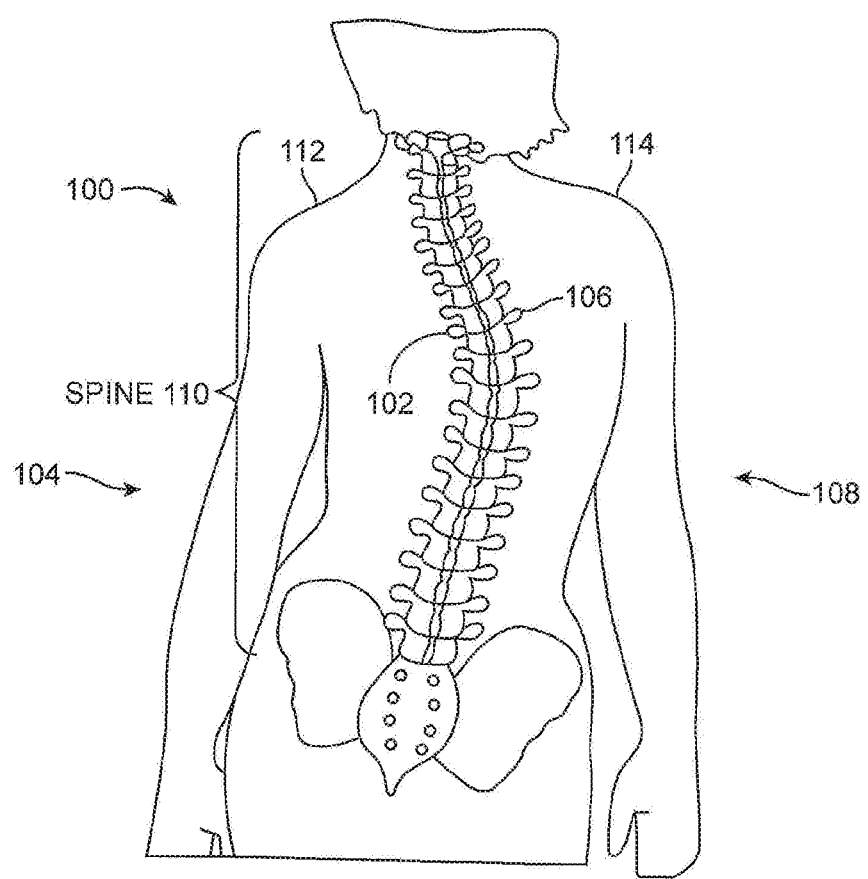
FIG. 1 illustrates the spine of a person with scoliosis.

FIG. 1 illustrates a patient 100 with scoliosis. The concave portion 102 of the spinal curve can be seen on the left side 104 of the patient 100, and the convex portion 106 can be seen on the right side 108 of the patient 100. Of course, in other patients, the concave portion 102 may appear on the right side 108 of the patient 100 while the convex portion 106 may be found on the left side 104 of the patient. In addition, as seen in FIG. 1, some rotation of the spine 110 is present, and unevenness between the left shoulder 112 and right shoulder 114 is seen.

Figure 2:
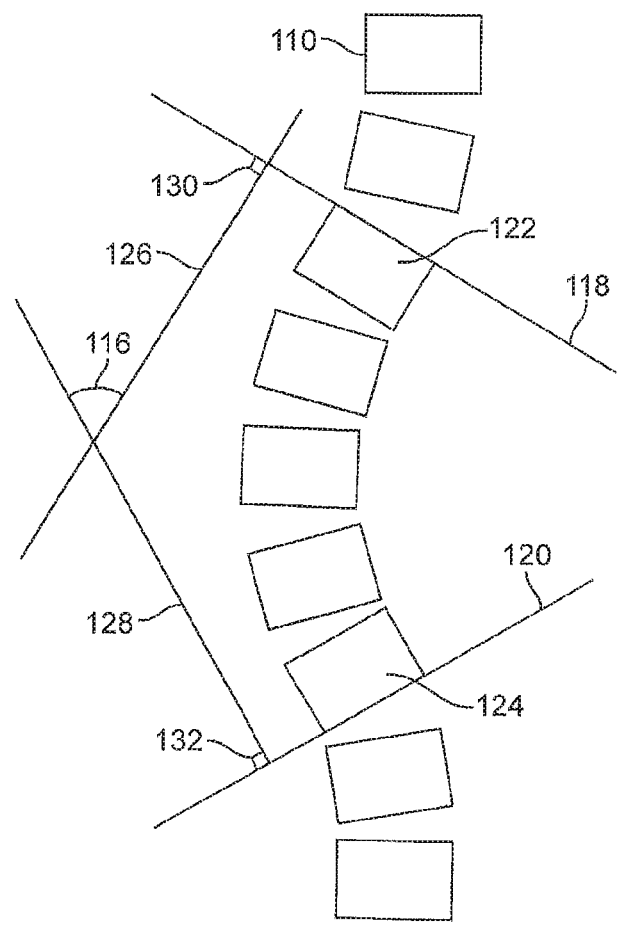
FIG. 2 illustrates the Cobb angle of a scoliotic spine.

FIG. 2 illustrates the Cobb angle 116 of a spine 110 of a patient with scoliosis. To determine the Cobb angle, lines 118 and 120 are drawn from vertebra 122 and 124, respectively. Intersecting perpendicular lines 126 and 128 are drawn by creating 90° angles 130 and 132 from lines 118 and 120. The angle 116 created from the crossing of the perpendicular lines 126 and 128 is defined as the Cobb angle. In a perfectly straight spine, this angle is 0°.

Figure 3:
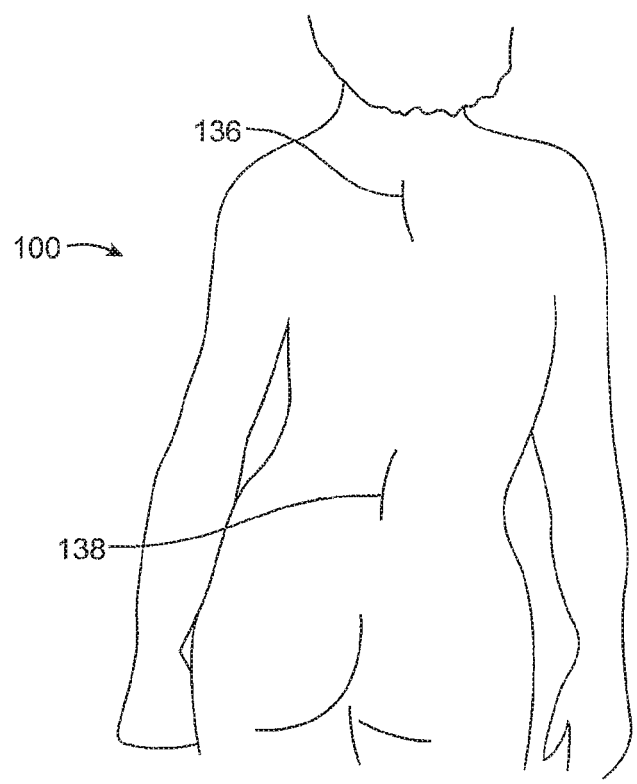
FIG. 3 illustrates the small incisions made during scoliosis non-fusion surgery of the inventive embodiments.

In many Adolescent Idiopathic Scoliosis (AIS) patients with a Cobb angle of 40° or greater, spinal fusion surgery is typically the first option. Alternatively, non-fusion surgery may be performed, for example with the distraction device 200 of FIG. 4. FIG. 3 illustrates an upper incision 136 and a lower incision 138 formed in the patient 100 which is typically made during non-fusion scoliosis surgery.

Figure 4:
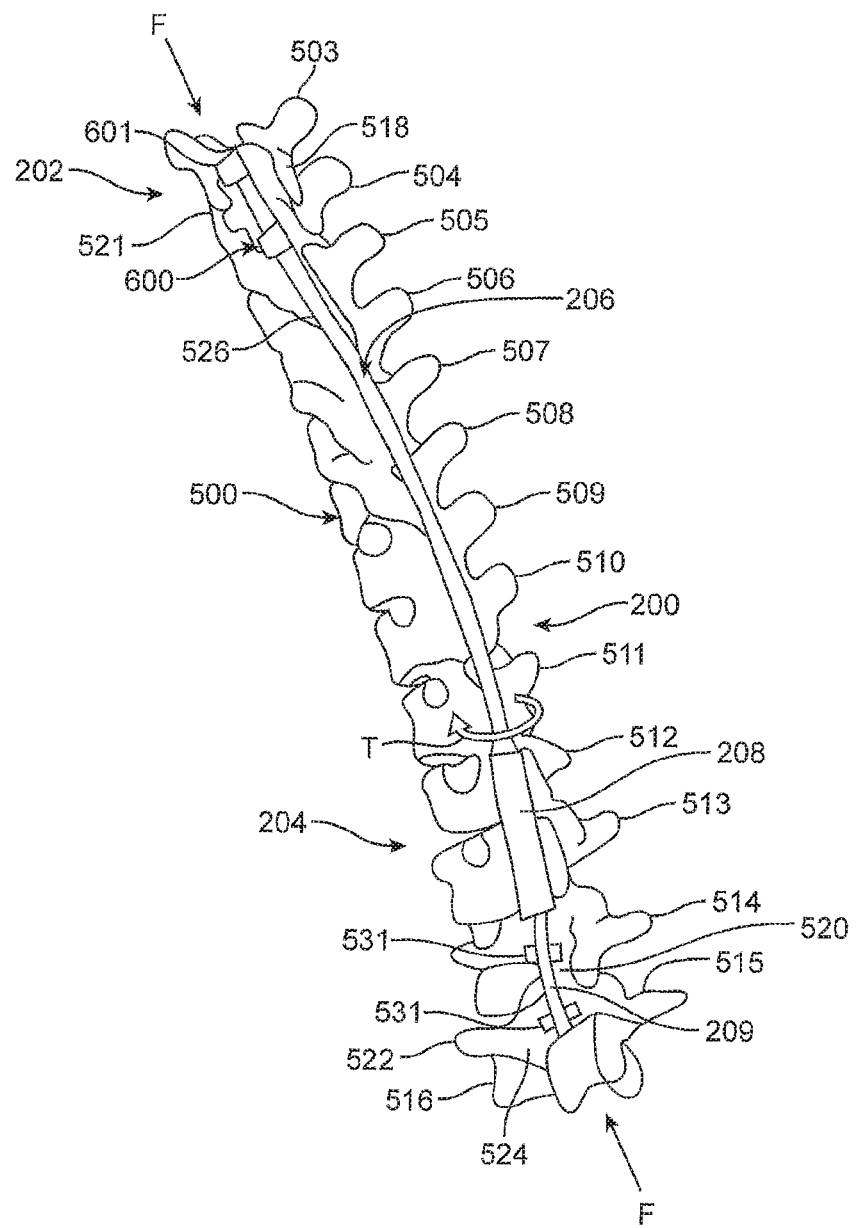
FIG. 4 illustrates an exemplary distraction device mounted on the spine of a subject.

FIG. 4 illustrates a distraction device 200 for treating scoliosis according to one embodiment of the invention. The distraction device 200, which is an implantable device, is fixated at its upper end 202 and lower end 204 to the patient's spine 500. The illustrated example of the spine 500 includes the particular thoracic and lumbar vertebrae that typically encompass a scoliotic curve, for example the curve of a patient with adolescent idiopathic scoliosis. The T3 through T12 thoracic vertebrae, 503, 504, 505, 506, 507, 508, 509, 510, 511, 512, respectively and the L1 through L3 vertebrae, 513, 514, 515 are depicted in FIG. 4, not in a severe scoliotic condition, but in a very slight residual curve that represents a modest curve that has been partially or completely straightened during the implantation procedure.

Each vertebra is different from the other vertebra by its size and shape, with the upper vertebra generally being smaller than the lower vertebra. However, generally, the vertebrae have a similar structure and include a vertebral body 516, a spinous process 518, 520, laminae 526, transverse processes 521, 522 and pedicles 524. In this embodiment, the distraction device 200 includes a distraction rod 206 which is adjustable (lengthwise) via a coupled adjustable portion 208. The distraction device 200 also includes a lower extension 209 which may be a short rod segment. The distraction device 200 is fixated to the spine 500 via hooks 600, 601 at the upper end 202 of the distraction rod 206. Alternatively, a clamp may be secured around an adjacent rib (not shown) or rib facet. In still another alternative, a pedicle screw system may be used.

Referring back to FIG. 4, the distraction device 200 is illustrated as being fixated to the spine 500 with a pedicle screw system 531, which attaches directly to the lower extension 209. The distraction rod 206 is shown after it has been bent into a kyphotic curve, and the lower extension is shown after it has been bent into a lordotic curve. As explained in more detail below. The adjustable portion 208 preferably contains a magnetic assembly having a permanent magnet configured to drive a lead screw that, depending on the direction of rotation of the internal magnet, will extend or retract the distraction rod 206 using the adjustable portion 208. Lengthening of the distraction rod 206, for example, will impart a distraction force to the spine 500. Retracting the distraction rod 206 will lower or remove the distraction force on the spine 500, for example if too high a distraction force causes pain or complications.

Because a scoliotic spine is also rotated (usually the center section is rotated to the right in AIS patients), the non-fusion embodiment presented here allows de-rotation of the spine 500 to happen naturally, because there is no fixation at the middle portion of the distraction device 200. In order to further facilitate this de-rotation, the distraction device 200 may allow for free rotation at its ends. For example, the adjustable portion 208 may be coupled to the spine via an articulating joint. U.S. Patent Application Publication Nos. 2009-0112207 and 2010-0094302, both of which are incorporated by reference, describe various articulating interfaces and joints that may be utilized to couple the adjustable portion 208 to the connecting rods or the like. These Published Applications further describe various distraction rod embodiments and methods of use that may be used with inventions described herein.

As noted, the distraction rod 206 and the lower extension 209 may be bent by the user (or supplied pre-curved) with the typical shape of a normal saggital spine, but it should also be noted that the curve may be slightly different than standard scoliosis fusion instrumentation, because in the non-fusion embodiment described herein, the distraction device 200 is not usually flush with the spine but rather is placed either subcutaneous or sub-fascial, and thus is not completely below the back muscles. In these less invasive methods, the only portions of the distraction device 200 that are designed to be placed below the muscles are the hooks 600, 601 and the portion of the distraction rod 206 immediately adjacent the hooks 600, 601, the pedicle screw system 531 and the lower extension 209. Thus, FIG. 4 illustrates an embodiment in which the bulk of the hardware associated with the distraction device 200 is placed over the muscle. It should be understood, however, that in alternative configurations, any other part of the entire implantable embodiment may be placed under the muscle (i.e., submuscular). It should be appreciated that a much smaller amount of muscle needs to be dissected during the procedure in comparison with current fusion procedures. This will allow for a much shorter procedure, much less blood loss, much quicker recovery, and less time in the hospital/less risk of infection.

Figure 5:
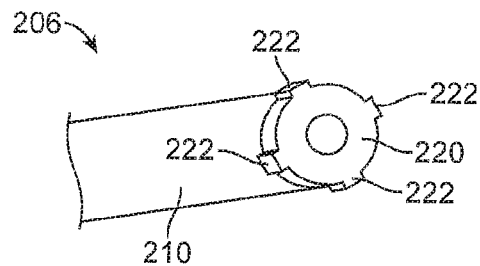
FIG. 5 illustrates a perspective view of one end of a distraction rod illustrating the splined tip.
Figure 6:
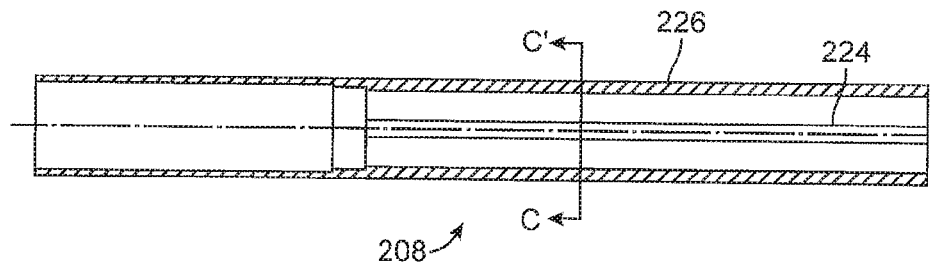
FIG. 6 is a side cross-sectional view of the tubular housing with the lead screw and magnetic assembly removed for clarity.
Figure 7:
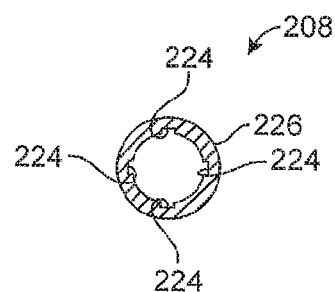
FIG. 7 is a cross-sectional view of the tubular housing taken along the line C-C in FIG. 6.

By design, the distraction rod 206 is configured to be distracted from the adjustable portion, increasing the total device length via magnetic adjustment. The preferred design for a distraction device 200, does not allow significant circumferential motion between the distraction rod 206 and the adjustable portion 208. FIG. 5 illustrates a perspective view of the splined tip 220 of the distraction rod 206. The splined tip 220 is illustrated with four (4) protrusions 222 that interface with four (4) corresponding longitudinal grooves 224 (two pairs in symmetric opposition) formed inside a tubular housing 226 (illustrated in FIGS. 6-7) of adjustable portion 208. The longitudinal grooves 224 may be formed by wire EDM machining or by broaching. While FIGS. 5-7 illustrate an embodiment that uses four (4) protrusions 222 along with four (4) longitudinal grooves 224 there may be more or fewer. The tight tolerance of the splined tip 220 with the longitudinal grooves 224 keeps the distraction rod 206 centered within the tubular housing 226. In addition, the combination of the splined tip 220 and corresponding grooves 224 act as an anti-rotation feature that prevents the distraction rod 206 from rotating relative to the tubular housing 226. This may be necessary to allow the distraction device 200 to be "rigidized" in the event the device is used in fusion applications, instead of the non-fusion applications described. For example, in a fusion application, it is desired that the spine 500 not be able to flex or rotate much during the months that the fusion is taking place. In either the fusion applications or the non-fusion applications, the anti-rotation features are intended to limit inadvertent extension and/or retraction of the distraction rod 206 resulting from, for instance, patient movements. Additional details may be found in U.S. Patent Application Publication No. 2012-0035661, which is incorporated herein by reference.

Figure 8:
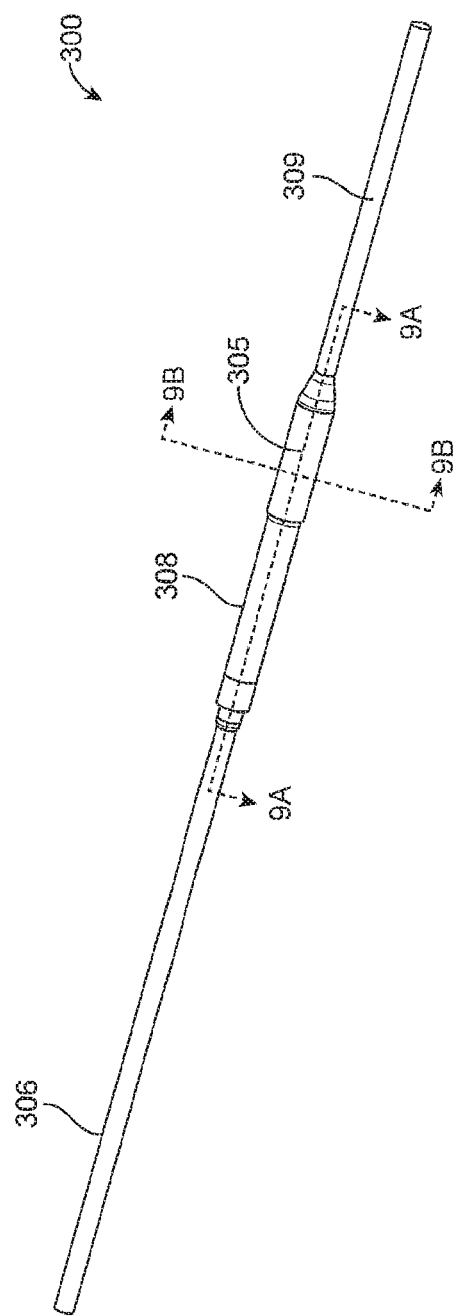
FIG. 8 illustrates an embodiment of a distraction device having a maintenance member.
Figure 9A:
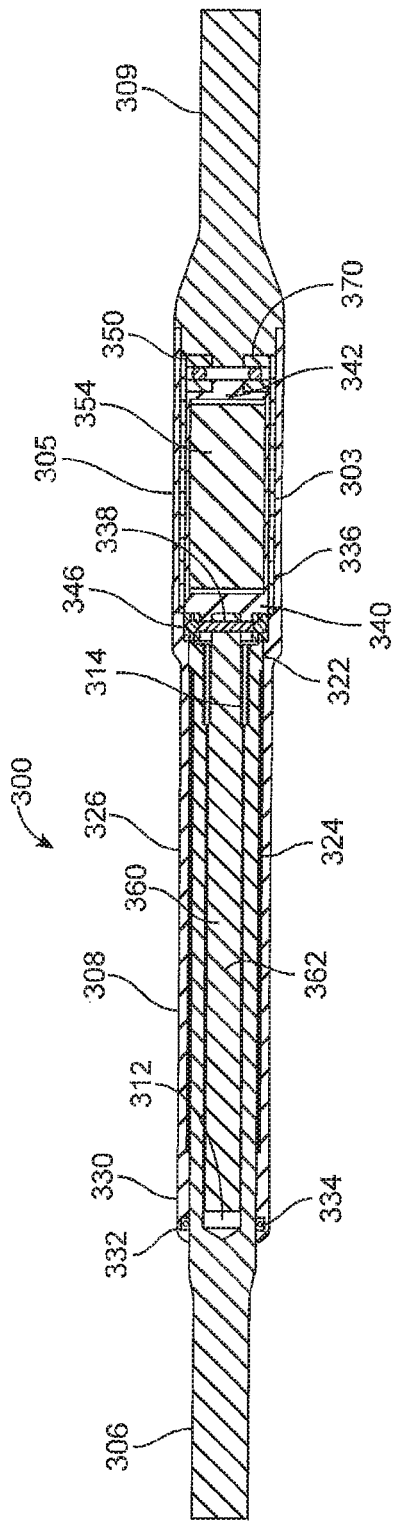
FIG. 9A illustrates a sectional view of the distraction device of FIG. 8 taken along the line 9A-9A.
Figure 9B:
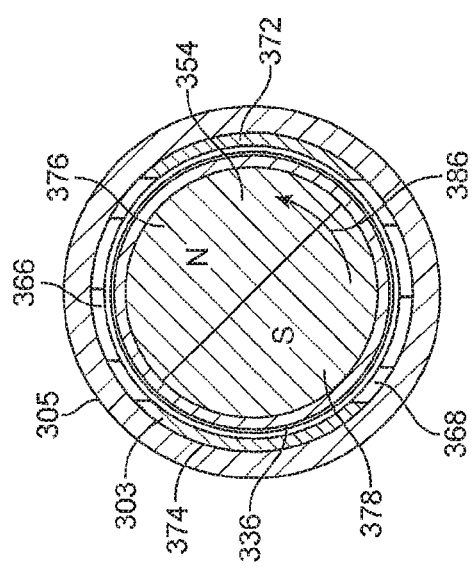
FIG. 9B illustrates a cross-sectional view of the distraction device of FIG. 8 taken along the line 9B-9B.

FIG. 8 is a view of a distraction device 300. Distraction device 300 has distraction rod 306 and adjustable portion 308. The distraction rod 306 moves axially relative to the adjustable portion 308 and the device is identical to the distraction device 200 described in FIG. 4. A lower extension 309 extends from the adjustable portion 308 in a direction opposite the distraction rod 306. FIG. 9A is a longitudinal section of the distraction device 300 of FIG. 8 taken along the line 9A-9A, while FIG. 9B is a cross-section of the same device taken along the line 9B-9B. Distraction rod 306 contains an elongate recess 312 as seen in FIG. 9A containing a nut 314 at its end. Also at the end of the distraction rod 306 are radial protrusions 322 which are configured to axially slide within longitudinal grooves 324 formed within a tubular housing 326 that forms part of the adjustable portion 308. O-ring gland 330 includes a recess 332 which contains an O-ring 334, forming a dynamic seal between the distraction rod 306 and the adjustable portion 308. In addition, the internal diameter of the O-ring gland 330 may be formed of a lubricious material, such as PEEK or ultra high molecular weight polyethylene, creating a cylindrical bearing surface for enlarged portion 331 of distraction rod 306 to slide. This can increase the distraction force of the distraction device 300 by minimizing the axial resistance. It can also minimize metal to metal particulate generation. Magnetic assembly 336 is rotatably held between a thrust bearing 350 and a radial bearing 346. The thrust bearing comprises two races with a plurality of balls in between. It is possible to have one of the races directly formed within the internal end of the extension 309, but a standard thrust bearing is depicted in FIG. 9A. Magnetic assembly 336 comprises a first cup 340 and a second cup 342 which adhesively contain a radially-poled cylindrical magnet 354. The magnetic assembly 336 is coupled to a lead screw 360 having external threads 362 which engage the internal threads of the nut 314. The lead screw may be made of titanium or titanium alloy, while the nut may be made of aluminum-bronze and they may both be coated with a biocompatible grease, such as Krytox, in order to minimize resistance. The radial protrusions 322 may alternatively be made as extensions of the nut 314, instead of as parts of the distraction rod 306. The magnetic assembly 336 is coupled to the lead screw 360 via a high strength pin 338. An expanded portion 305 of tubular housing 326 is configured to rotatably contain the magnetic assembly 336. The tubular housing 326 is secured to the extension 309, for example, by a circumferential weld. As the magnetic assembly 336 is turned non-invasively by an externally applied rotating magnetic field, the lead screw 360 is forced to turn within the nut 314, causing the distraction rod 306 to axially displace with relation to the adjustable portion 308.

Figure 10:
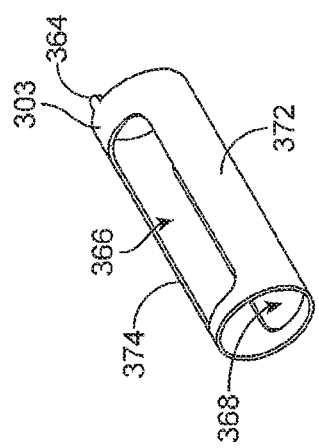
FIG. 10 illustrates a cylindrical maintenance member from the distraction device of FIGS. 8, 9A, and 9B.

Annularly contained between the magnetic assembly 336 and the expanded portion 305 of the tubular housing 326 is a cylindrical maintenance member 303 made from a magnetically permeable material, such as 400 series stainless steel. The cylindrical maintenance member 303 can be seen in isolation in FIG. 10. The cylindrical maintenance member 303 has two tabs 364 (one such tab is hidden from view in FIG. 10) radially opposed at one end. The tabs 364 are configured to engage into recessed areas 370 at the base of extension 309, within the interior of the adjustable portion 308. This allows the cylindrical maintenance member 303 to remain non-rotatable or stationary with respect to the tubular housing 326 and the extension 309. The cylindrical maintenance member 303 comprises first and second side walls 372, 374, having first and second cut outs 366, 368 arrayed between them. When the distraction device 300 is not being adjusted, the magnetic poles 376, 378 of the radially-poled cylindrical magnet are magnetically attracted to the first and second side walls 372, 374 of the cylindrical maintenance member 303 and tend to align with the first and second side walls 372, 374. However, when the magnetic assembly 336 is forced to rotate due to the effect of a sufficiently large rotating magnetic field on the radially-poled cylindrical magnet 354, the magnetic assembly 336 overcomes the smaller attractions of the first and second side walls 372, 374. FIG. 9B shows the magnetic assembly 336 actively being turned in the direction or arrow 386. The poles 376, 378 of the radially-poled cylindrical magnet 354 are not shown as being aligned with the first and second side walls 372, 374. However, when the large rotating magnetic field is removed, the poles 376, 378 will align with the first and second side walls 372, 374. The magnetic attraction between the poles 376, 378 and the first and second side walls 372, 374 serves to maintain the specific amount of distraction length achieved in the distraction device 300, even as patient makes variable torsional, and compressive motions (left, right extend, contract). The advantage of this design is that the distraction device 300 is capable of being distracted, and if it is over distracted, for example if it causes the patient pain or discomfort, it can be shortened. However, this free two-directional capability does not interfere with the stability of the distraction length, because of the magnetic maintenance enabled by the first and second side walls 372, 374 of the cylindrical maintenance member 303. Representative dimensions include about 0.280 inches for the diameter of the radially-poled cylindrical magnet 354; about 0.305 inches for the outer diameter of both the first cup 340 and the second cup 342; about 0.325 inches for the inner diameter of the cylindrical maintenance member 303; and about 0.015 inches for the wall thickness of the cylindrical maintenance member 303.

Figure 11:
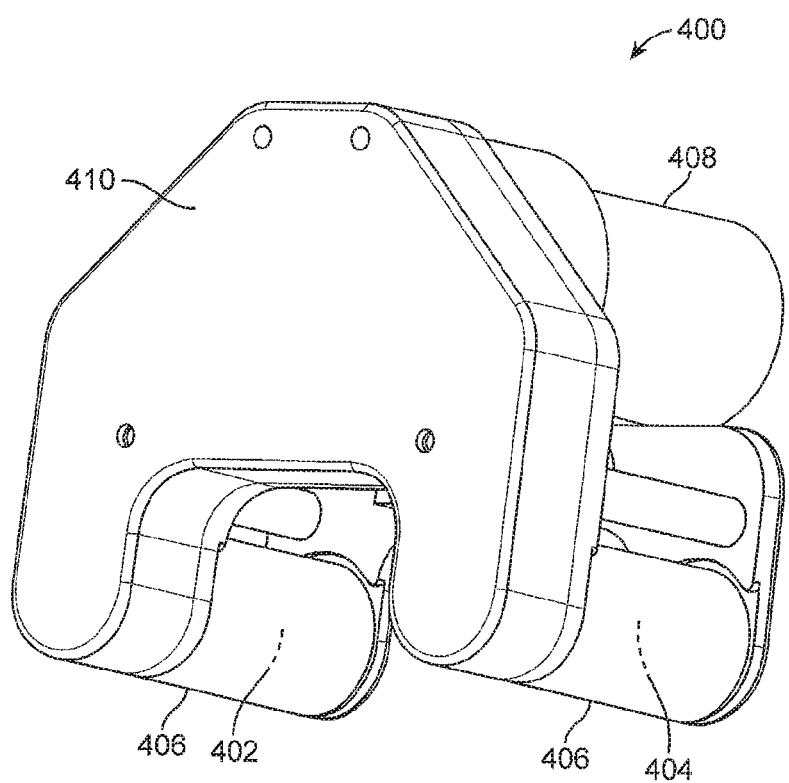
FIG. 11 illustrates an external adjustment device that is used with the distraction devices described herein.

FIG. 11 illustrates an external adjustment device 400 according to one embodiment that includes two permanent magnets 402, 404 contained within respective covers 406. Each permanent magnet 402, 404 is rotatable within its respective cover 406 and provides a moving magnetic field. A motor 408 is mechanically engaged to the permanent magnets 402, 404 via a transmission (not shown) contained within a housing 410 of the external adjustment device 400

FIG. 12 illustrates another embodiment of a distraction device 700 having a first distraction rod 701 and a second distraction rod 706, a first adjustable portion 707, and a second adjustable portion 708. Distraction rods 701, 706 have respective ends 717, 719 configured for attachment to spine by known methods such as pedicle screws or hooks. Located in between the two adjustable portion 707 and 708 is an adjustable joint 711. A detail of adjustable joint 711 in FIG. 13 shows a first interfacing surface 713 and a second interfacing surface 715. Each interfacing surface 713, 715 contains several circumferentially arrayed teeth 721 as seen in FIG. 14, that allow the two interfacing surfaces 713, 715 to engage with each other at a range of possible angular orientations. The angle 723 can be made variable over a wide range of positive and negative angles (e.g., 90° or more), though in practice, a much smaller range is needed. The chosen angle can be locked by tightening a locking member 725 such as a securing screw. The angle 723 may, for example, be chosen to match the current kyphosis (sagittal plane) of a patient, or the desired thoracic kyphosis through treatment. For example, an angle within the normal range of 20° to 50° may be used. Alternatively, if the patient is hyperkyphotic or hypokyphotic, the particular angle of kyphosis, outside the normal range, may be chosen. Each adjustable portion 707, 708 may be independently lengthened, using the magnetic lengthening technique described herein. It may be desirable to lengthen one of the sides of the distraction device 700 and not the other. For instance, first distraction rod 701 may be extended from the first adjustable portion 707 while the second distraction rode 706 may not move relative to the second adjustable portion 708. Alternatively, by adjusting both sides (707, 708) equally, the apex thoracic kyphosis may be maintained at the same level of the spine. By lengthening the side towards the head more than the side towards the feet, the apex of the thoracic kyphosis may be moved towards a lower area of the spine. By lengthening the side towards the feet more than the side towards the head, the apex of the thoracic kyphosis may be moved towards an upper area of the spine. Furthermore, by lengthening the side towards the head and shortening the side towards the feet, the apex of the thoracic kyphosis may be more drastically moved towards a lower area of the spine, and by lengthening the side towards the feet and shortening the side towards the head, the apex of the thoracic kyphosis may be more drastically moved towards an upper area of the spine.

The distraction device 700 of FIG. 12 contains other features that make it appropriate for use as a temporary rod, in gradually correcting a sagittal (hyperkyphosis, hypokyphosis) or coronal (scoliosis) deformity in a patient with a mature spine. The two adjustable portions 707, 708 allow 70 mm each of axial lengthening and so together allow for a total of 140 mm of lengthening. If the spine were to be significantly distracted manually (without the magnetic actuation) at the implant surgery, then this amount of total lengthening would probably not be needed. In growing patients, the magnetic actuation is intended to correspond with growth. However, in a no longer growing patient, and particularly in a patient whose treatment regime would benefit from gradual distraction, the axial lengthening is intended to partially or substantially straighten a curved spine, would often require a total distraction length as long as 140 mm, and even as high as 240 mm in a large patient with a severe deformity (greater than 90°). In addition to the length required in the axial distraction to make a curve spine straight, there will actually be additional length that will often need to applied, in order to overstrain and permanently stretch ligaments of the vertebrae. In some cases, these ligaments may require as much as 30% or even 50% additional strain in order to permanently change their length as desired. This is analogous to the stretching done on ligaments and other soft tissue in joint splinting applications. The mechanism for ligament stretching can be stress relaxation and viscoelasticity of the soft tissue and even some micro cracking or "neck down." The adjustable portions 707, 708 in the distraction device 700 also have planetary gearing 727 disposed between the magnetic assembly 736 and the lead screw 760 (illustrated only in adjustable portion 707 in FIG. 12). The gearing 727 allows for a significantly higher distraction force to be placed on the spine. In the mature spine patients, the spine is often stiffer, and requires significantly more force than when distracting an immature spine. Depending on the patient, forces as hiCgh as 112 pounds (500 Newton) or higher may be required to significantly cause stretching of spinal ligament groups. Gear ratios of 4:1, 16:1 and 64:1, for example, from one, two, or three sets of planetary gears, can be incorporated in order to multiply the deliverable distraction force by close to four, sixteen or sixty four times. In an assembly with three 4:1 planetary gear sets, with a total gear ratio of 64:1, the magnetic assembly would make sixty four rotations for every one rotation of the lead screw. In keeping with the gradual distraction treatment methodology, the distraction device 700 may be positioned in patient during implantation surgery so that the angle is oriented in a plane which is between the sagittal and coronal plane, allowing it to in part match the contours of the patients current or desired kyphotic curve, but also, to fit on a spine that has a residual scoliotic curve.

Figure 15:
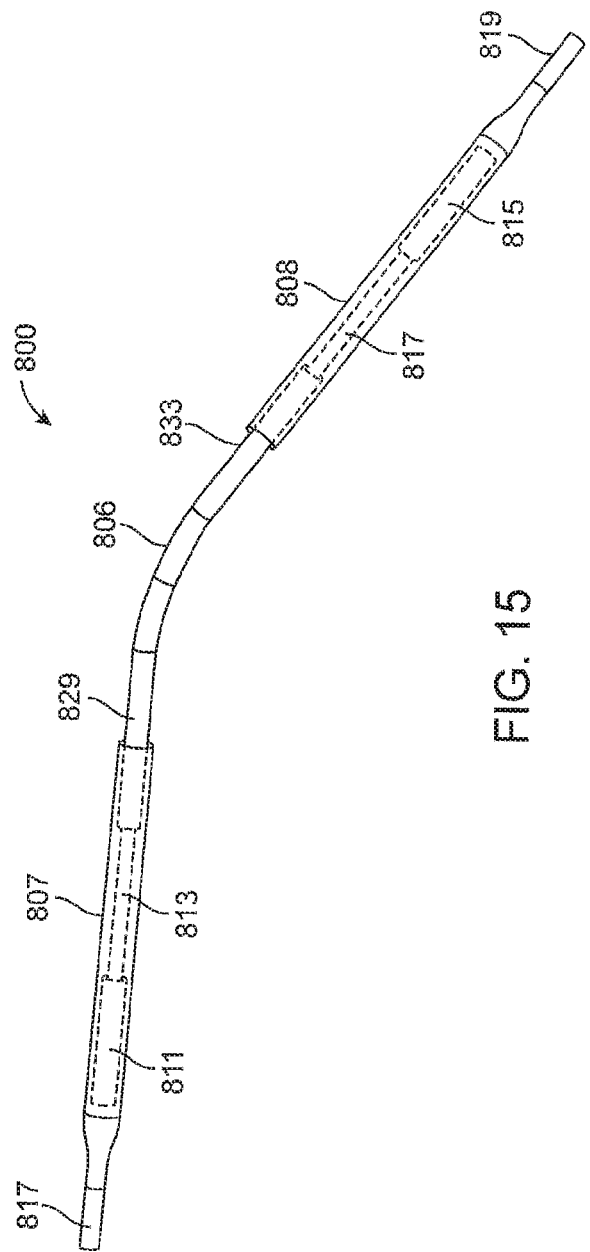
FIG. 15 illustrates a distraction device having a bendable section between two actuators.

Turning now to FIG. 15, another embodiment of a distraction device 800 having a single, central distraction rod 806 is depicted. Two adjustable portions 807, 808 are coupled to the commonly shared distraction rod 806. Adjustable portion 807 is coupled to a first end 829 of the distraction rod 806 while adjustable portion 808 is coupled to the opposite end 833 of distraction rod 806. More specifically, adjustable portion 807 includes a rotatable magnetic assembly 811 that is coupled to a lead screw 813 that interfaces with a threaded portion located inside the first end 829 of the distraction rod 806. For example, as explained in other embodiments, a nut having internal threads may be disposed in a recess of the first end 829 of the distraction rod 806 and may interface with the lead screw 813. Likewise, adjustable portion 808 includes a rotatable magnetic assembly 815 that is coupled to a lead screw 817 that interfaces with a threaded portion (e.g., threaded nut as described above) located inside the second end 833 of the distraction rod 806. As in FIG. 14, ends 817, 819 are configured for attachment to spine by known methods such as pedicle screws or hooks. However, in distraction device 800, ends 817, 819 extend from adjustable portions 807, 808, as opposed to extending from a distraction rod. The distraction rod 806 may be supplied to the surgeon with a typical sagittal curve, for example a typical thoracic kyphosis. Alternatively, the distraction rod 806 may be supplied straight, and may be bent to a desired curve by the surgeon, using a French bender or in situ benders. The distraction rod 806 may also be supplied to the surgeon in a first curved shape, and may be modified by the surgeon into a second curved shape. An advantage to both the distraction device 700 of FIG. 12 and the distraction device 800 of FIG. 15 is that the total length of the non-bendable or non-angulating portions (essentially the adjustable portions 707,708 or 807,808) can be shorter. For example, if the distraction device 800 of FIG. 15 had a single 90 mm long adjustable portion capable of lengthening 48 mm it might be considered to be too long and straight at the adjustable portion for a certain group of patient anatomies. However, if this device were instead made with two adjustable portions, for example 66 mm long each, with the curved or bendable distraction rod 806 in between, and each adjustable portion were capable of 24 mm of lengthening, the device would more acceptably contour to these patients' anatomies. In use, instead of lengthening the single actuator 4 mm, for example, the physician might lengthen each actuator 2 mm, for 4 mm total.

Figure 16:
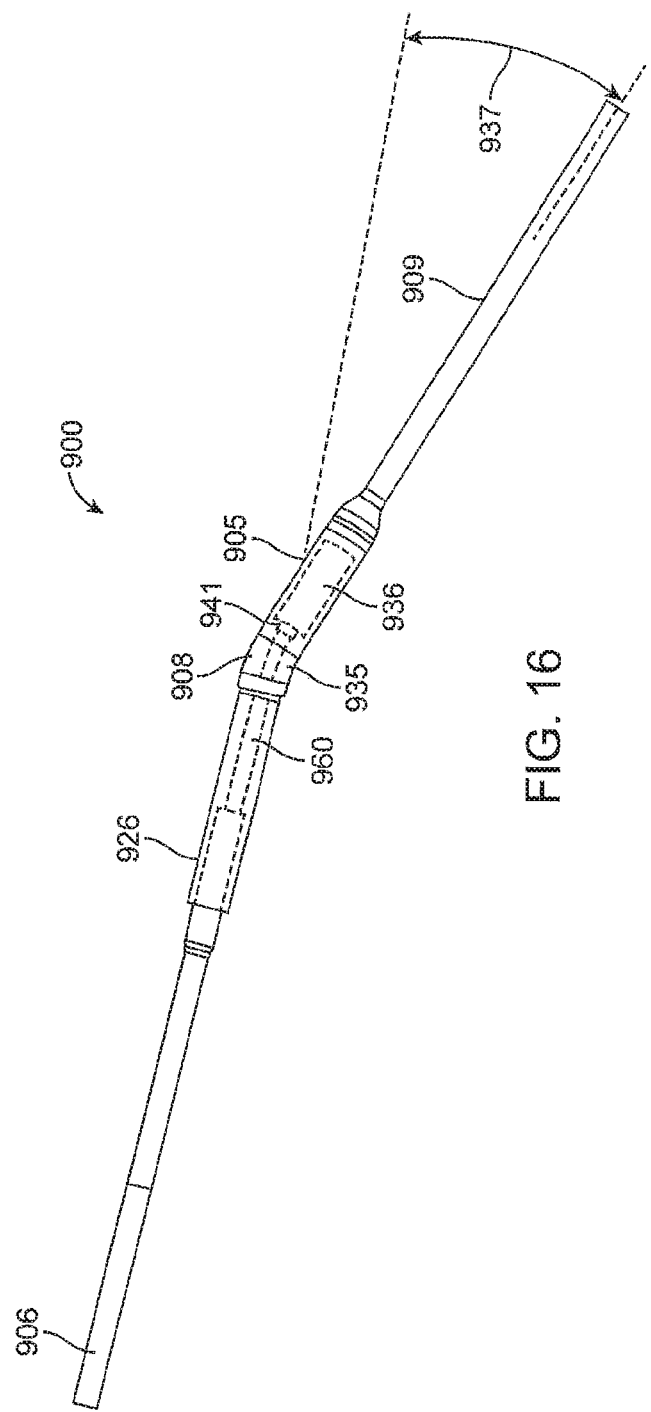
FIG. 16 illustrates a distraction device having an actuator with an angled shape.

Distraction device 900 in FIG. 16 has a single adjustable portion 908 which is configured in a permanently curved or angled shape. Alternatively, this adjustable portion 908 may actually be made of a bendable tube. The permanently curved or angled adjustable portion 908 comprises a tubular housing 926 and an expanded portion 905. In the embodiment specifically depicted, an intermediate tubular section 935 is welded to both the tubular housing 926 and the expanded portion 905. Distraction rod 906 actuates axially within adjustable portion 908. Extension 909 is coupled to adjustable portion 908 at the other end. The device may be supplied with angle 937 of between 3° and 35°, and more particularly, with an angle 937 of about 10°. This angle again, depending upon the use of the device, may be oriented on the patient completely within the sagittal plane, or between the sagittal and coronal planes. As seen in FIG. 16, the rotatable magnetic assembly 936 is disposed in the tubular section 935 and is coupled to a lead screw 960 via a universal joint 941 (described in more detail below). The lead screw 960 interfaces with the distraction rod 906, for example, a threaded nut or the like as described elsewhere herein. Rotation of the magnetic assembly 936 causes lead screw 960 to rotate which then translations into axial, telescopic movement of the distraction rod 906 relative to the housing 926.

Figure 17A:
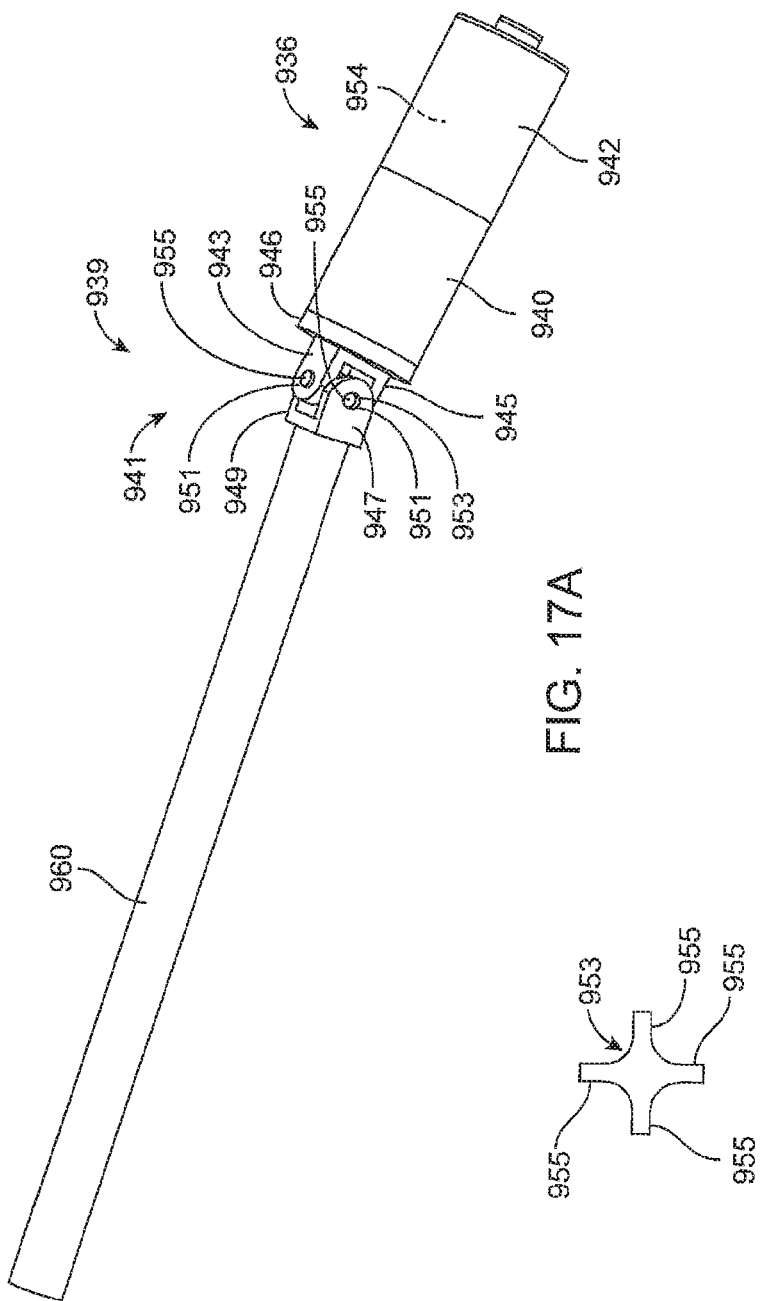
FIG. 17A illustrates the internal drive structure of the distraction device of FIG. 16, incorporating a universal joint.
Figure 17B:
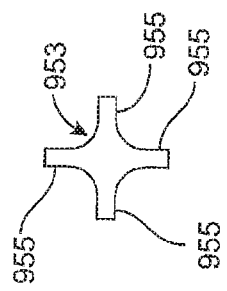
FIG. 17B illustrates a cross structure used as part of a universal joint.

FIG. 17A illustrates an internal assembly 939 of the distraction device 900 of FIG. 16. Magnetic assembly 936 comprises first cup 940 and second cup 942, which adhesively contain a radially-poled cylindrical magnet 954. The magnetic assembly 936 is configured for rotation via a radial bearing 946 at one end and a thrust bearing (not shown) at the other end. The radial bearing 946 is placed annularly around a smaller diameter extension of the first cup 940. The magnetic assembly 936 is coupled to a lead screw 960 by a universal joint 941, which is constructed as follows. Extending from the smaller diameter extension of the first cup 940 are two tabs 943, 945. Also extending from the end of the lead screw 960 are two tabs 947, 949. Each of the four tabs 943, 945, 947, 949 has a through hole 951. A cross 953, as best seen in FIG. 17B, consisting of four ends 955 separated by 90° each couples the tabs 943, 945 of the first cup 940 to the tabs 947, 949 of the lead screw 960, the ends 955 each passing through one of the through holes 951 so that the magnetic assembly 936 and the lead screw 960 remain secured to each other, while the ends 955 are free to angularly displace within the through holes 951. This allows a torque placed on the magnetic assembly 936 to be transferred with very good efficiency to the lead screw 360, even though they are not both oriented along the same axis.

Figure 17C:
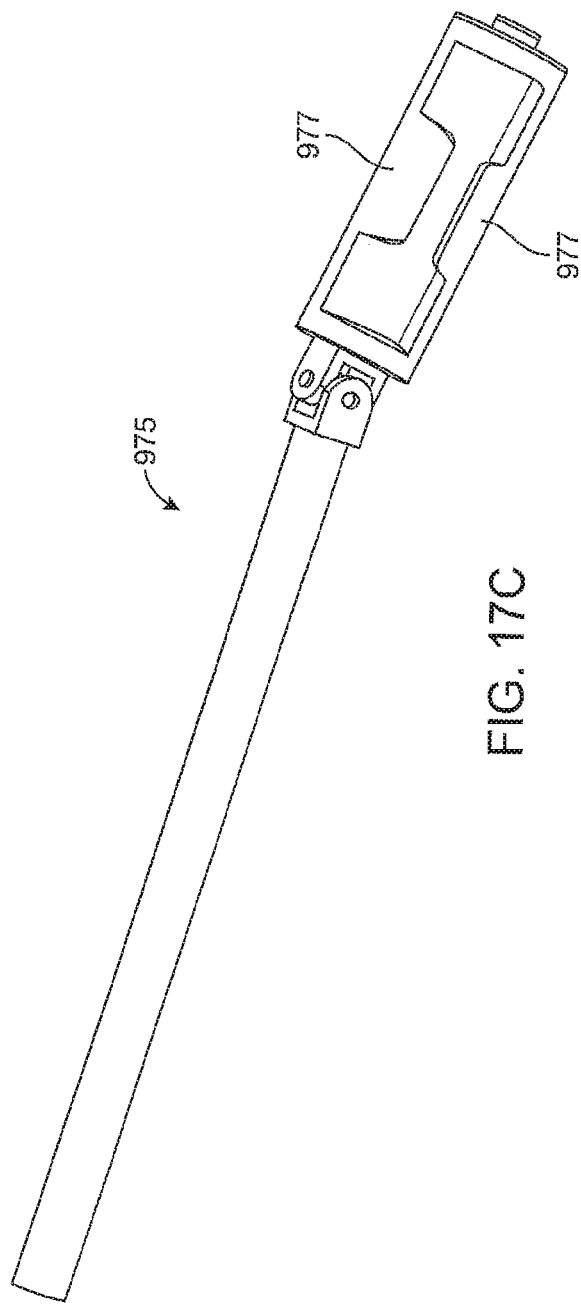
FIG. 17C illustrates an alternative magnetic assembly.
Figure 19:
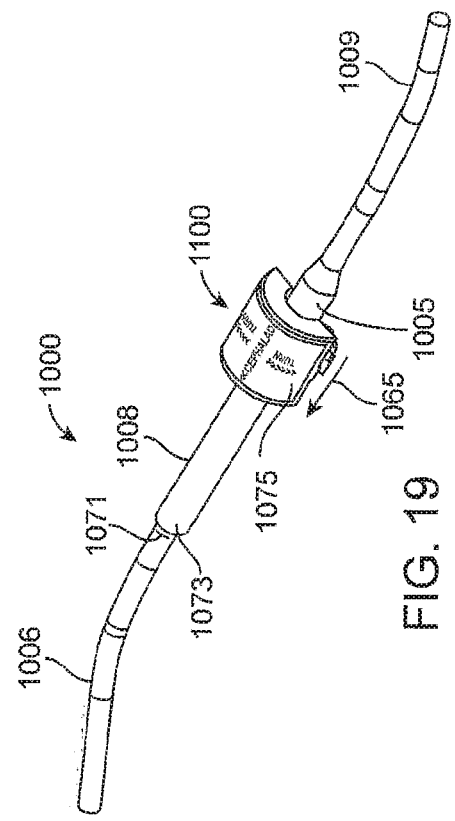
FIG. 19 illustrates a manual distraction tester placed upon a distraction device.
Figure 18:
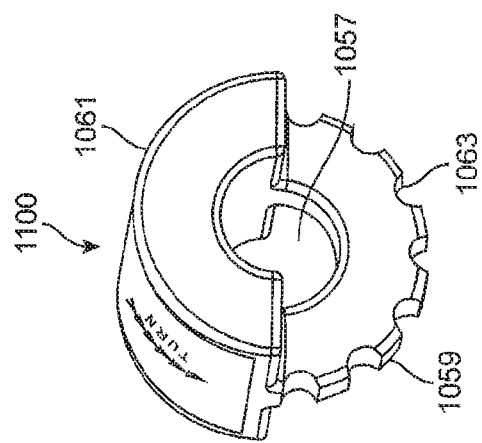
FIG. 18 illustrates a manual distraction tester.

While FIG. 17A illustrates a magnetic assembly 936 that includes a magnet 954, in other alterative embodiments, the magnetically assembly does not need to include a magnet. Instead, as seen in FIG. 17C, a magnetic assembly 975 may include circumferentially arrayed magnetically permeable elements 977, for example 400 series stainless steel components. These circumferentially arrayed magnetically permeable elements 977 can be arrayed in such a way so that they are also magnetically drivable by a rotating magnetic field (e.g., arrayed at one or more circumferential locations about a common axis of rotation). A magnetic assembly 975 may even include only one magnetically permeable element 977 if, for example, either two external adjustment devices 400 are used; a first external adjustment device 400 located on a first side of the patient and a second external adjustment device 400 located on a second side of the patient, so that the first external adjustment device 400 turns the magnetic assembly 975 over an arc of 180° and the second external adjustment device 400 turns the magnetic assembly 975 over another 180°. Alternatively, a single external adjustment device 400 may be configured that turns at least one magnet located on a first side of the patient while also turning a second magnet located on a second side of the patient. As still another alternative, the magnetic assembly may be replaced by a motor which is configured to drive the screw. The motor may be powered by an implantable battery, or may be powered (and controlled) via an inductive coupling, for example a coupling that allows a capacitor to be charged non-invasively.

FIGS. 18-21 illustrate a manual distraction tester 1100 configured for placement over a distraction device 1000 having a distraction rod 1006, an adjustable portion 1008, and expanded portion 1005 and an extension 1009. The use of this manual distraction tester removes the need to use the actual external adjustment device 400 to test the distraction device 1000 during the implantation surgery. The manual distraction tester 1100 has a body portion with a hollow cylindrical cavity 1057 (seen in FIG. 18) there through which is sized for placing over the expanded portion 1005 of the distraction device 1000. For example, if the expanded portion 1005 has a diameter of 10.5 mm, the hollow cylindrical cavity 1057 may have a diameter of 11.0 mm for clearance. The manual distraction tester 1100 has a minimally magnetic circumferential portion 1059, and a maximally magnetic circumferential portion 1061. The minimally magnetic circumferential portion 1059 and the maximally magnetic circumferential portion 1061 are spaced apart from one another about the periphery of the body of the manual distraction tester 1100. The maximally magnetic circumferential portion 1061 is configured to attract one of the poles of the implanted magnet of the distraction device, while the minimally magnetic circumferential portion 1059 is configured to either not attract a magnetic pole at all, or to attract a pole significantly less than the maximally magnetic circumferential portion 1061, so that the attraction of the pole by the maximally magnetic circumferential portion 1061 dominates.

As illustrated, the entire body of the manual distraction tester 1100 is monolithic and configured from a single material, for example 420 stainless steel, although other materials having magnetic permeability may be used. Thought the minimally magnetic circumferential portion 1059 has some attraction to magnet poles, the significantly larger mass of the maximally magnetic circumferential portion 1061 dominates. One way to achieve the difference in magnetic attraction between the two circumferential portions, if the manual distraction tester 1100 is made entirely from 420 stainless steel, is to make, for example the axial thickness of the minimally magnetic circumferential portion 1059 small (for example 2.5 mm) and the axial thickness of the maximally magnetic circumferential portion comparatively large (for example 19 mm). The manual distraction tester 1100 is axially slid onto the distraction device 1000 in the direction of the arrow 1065 in FIG. 19, and the maximally magnetic circumferential portion 1061 immediately orients with a pole of the radially-poled cylindrical magnet (not shown) within the expanded portion 1005 of the distraction device 1000. Alternatively, the manual distraction tester 1100 may be placed onto the distraction device 1000 from the other end. The manual distraction tester has knurls 1063 which aid in rotating it by hand.

Figure 21:
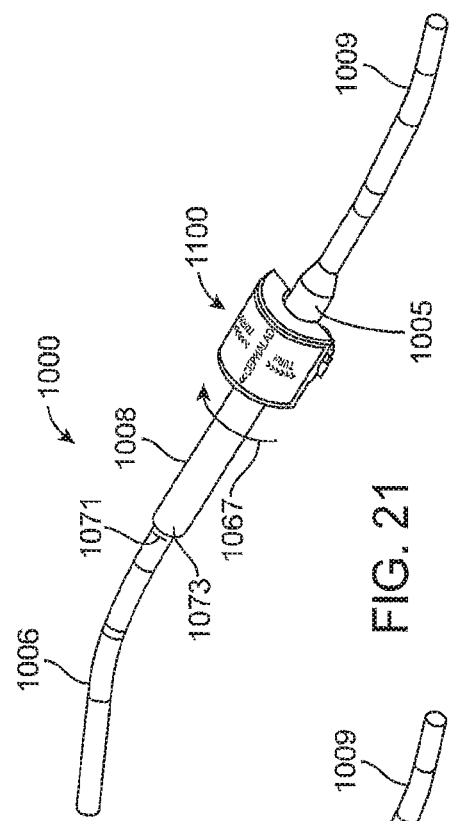
FIG. 21 illustrates a manual distraction tester being turned in a second direction.
Figure 20:
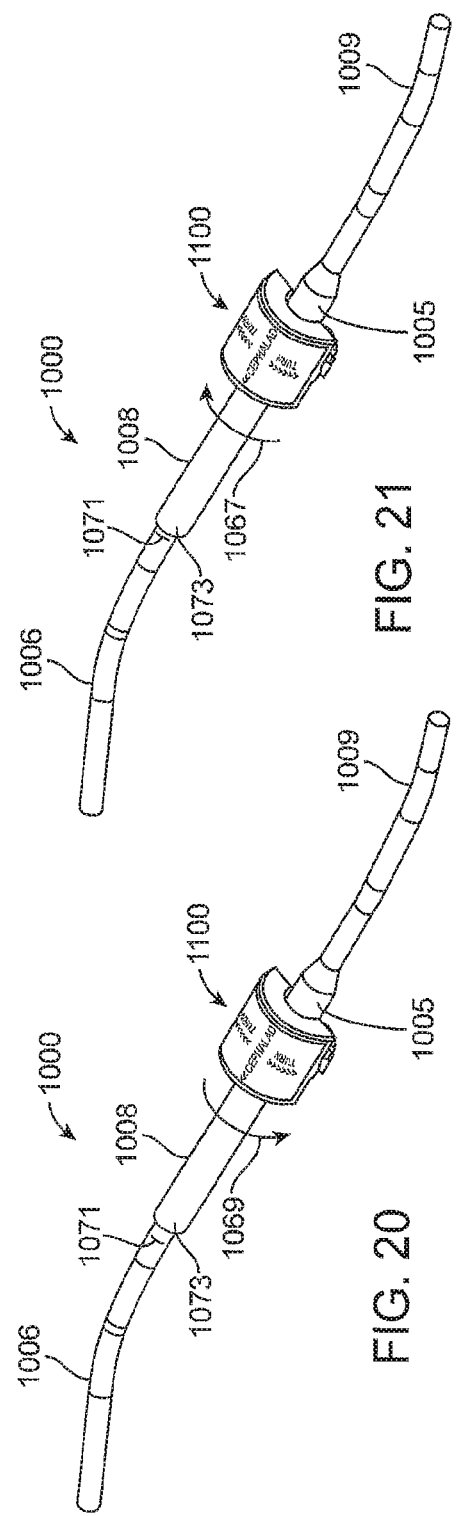
FIG. 20 illustrates a manual distraction tester being turned in a first direction.

The manual distraction tester 1100 is turned in a first direction 1069, magnetically causing the radially-poled cylindrical magnet to turn and in turn to cause lengthening of the distraction device 1000. A mark 1071 on the distraction rod 1006 can easily be seen moving in relation to an end 1073 of the adjustable portion 1008 of the distraction device 1000. FIG. 20 shows the manual distraction tester 1100 being turned in a first direction 1069 and the mark 1071 displaced axially to indicate that lengthening is correctly occurring, and that functionality has been confirmed. FIG. 21 shows the manual distraction tester 1100 then being turned in a second direction 1067, causing the distraction device 1000 to shorten. The mark 1071 has returned to its original position. The mark may be placed on the distraction rod 1006 by laser marking technique, printing or equivalent methods. A face 1075 of the manual distraction tester 1100 has markings which show, for example, the correct orientation at which the manual distraction tester 1100 should be placed, for example an arrow pointing cephalad (towards the head of the patient), the rotation to turn in order to lengthen the distraction device 1000, and the direction to turn in order to shorten the distraction device 1000. These may also be laser marked or printed. Alternative to the construction shown, it is also contemplated to make the manual distraction tester from a non-magnetic frame (such as nylon, PEEK, titanium, ABS, or a polymer) with a large piece of magnetic material (such as 420 stainless steel) attached at the maximally magnetic side 1061. The manual distraction tester 1100 may be coated on the hollow cylindrical cavity 1057 surface, to aid in its ability to smoothly slide or turn, without scratching the distraction device 1000.

A distraction rod 1206 is shown in FIGS. 22-24 which includes a nut 1214 having an internal thread 1277. Nut 1214 is axially maintained within distraction rod 1206 by flange 1279 which is within cavity 1281. Both flange 1279 and cavity 1281 may optionally extend 360° around nut 1214 and distraction rod 1206 respectively. Distraction rod 1206 has a plurality of protrusions 1222a (e.g., four) which are configured to slide axially within longitudinal grooves of the housing holding the rotatable magnetic assembly (e.g., longitudinal grooves 224 of FIG. 6 or longitudinal grooves 324 of FIG. 9A). Nut 1214 also has four protrusions 1222b which are also configured to slide axially within longitudinal grooves 224, 324. Internal thread 1277 is configured to interface with external thread 362 of lead screw 360. As seen in FIG. 24, at the respective ends of internal thread 1277 is a first collar 1283 and a second collar 1285. The first and second collars 1283, 1285 are disposed on opposing sides of the internal thread 1277 of the nut 1214. The inner diameter of first and second collars 1283, 1285 is approximately equal to the major diameter of the internal thread 1277. When external thread 362 of lead screw 360 is engaged with internal thread 1277 of nut 1214 and the patient is not being lengthened, the first and second collars 1283, 1285 serve to minimize the ability of the nut 1214 to "walk" along lead screw 360 when the patient moves (either compressing, tractioning or torsioning rod). However, lead screw 360 and nut 1214 do not dig into each other, because nut 1214 retains some free movement because of gap 1287 between the outer diameter 1289 of nut 1214 and inner bore diameter 1291 of distraction rod 1206.

When adjusting the length of the distraction device, the lead screw 360 turns within nut 1214 because protrusions 1222a of distraction rod 1206 and protrusions 1222b of nut 1214 are held within longitudinal grooves 224, 324 of the housing and so they remain rotationally static with respect to adjustable portion 308, while allowing distraction rod 1206 to axially adjust in relation to adjustable portion 308. This collared nut 1214 allows a stability of the distraction length of the distraction device that precludes the need for the cylindrical maintenance member 303 of FIGS. 9A, 9B, and 10. In less demanding applications, a simpler version of the nut 1214 may be used, wherein the nut 1214 has the inner thread 1277, first collar 1283 and second collar 1285, but is permanently bonded (with epoxy for example) within the inner bore diameter 1291 of distraction rod 1206. In such an embodiment, there is no gap 1287.

While embodiments have been shown and described, various modifications may be made without departing from the scope of the inventive concepts disclosed herein. The embodiments have application in many other medical conditions, including lengthening of bones by intramedullary placed distraction devices or by distracting plates placed on the exterior of bones. The invention(s), therefore, should not be limited, except to the following claims, and their equivalents.

The invention claimed is:

1. A distraction system comprising:
   an adjustable portion having a first portion separated from a second portion by an intermediate portion, wherein the second portion has a larger diameter than the first portion;
   an extension rod extending from the second portion;
   a distraction rod configured to telescope within the first portion;
   a first rotatable assembly disposed within the second portion and coupled to a universal joint; and
   a lead screw coupled to the universal joint and interfacing with the distraction rod,
   wherein the distraction system is configured such that rotation of the rotatable assembly causes rotation of the universal joint which causes rotation of the lead screw, which causes the distraction rod to move relative to the adjustable portion,
   wherein a curve of the adjustable portion defines an angle between the first portion and the second portion, wherein the angle is between 3° and to about 35°, and
   wherein the curve of the adjustable portion defining the angle is permanent.

2. The distraction system of claim 1, the universal joint comprising:
   a first tab and a second tab coupled to the rotatable magnetic assembly; and
   a third tab and a fourth tab coupled to the lead screw;
   the first tab and the second tab coupled to the third tab and the fourth tab by a cross, the universal joint configured to transfer torque placed on the magnetic assembly to the lead screw.

3. The distraction system of claim 1, the rotatable assembly comprising a magnet.

4. The distraction system of claim 1, wherein the adjustable portion comprising a housing, and the distraction rod is configured to telescope within the housing of the adjustable portion.

5. The distraction system of claim 1, wherein the adjustable portion comprising a housing, and the distraction rod is positioned axially centered within the housing.

6. The distraction system of claim 1, wherein the first portion and the second portion are straight and the curve of the adjustable portion is defined by the intermediate portion, and wherein the adjustable portion has a tubular housing.

7. The distraction system of claim 1,
wherein a first portion of the lead screw is disposed within the first portion of the adjustable portion;
wherein a second portion of the lead screw is disposed within the intermediate portion of the adjustable portion; and
wherein a third portion of the lead screw is disposed within the second portion of the adjustable portion.

8. The distraction system of claim 1, wherein the rotatable assembly comprises:
a first cup;
a second cup; and
a radially poled cylindrical magnet disposed between and partially within each of the first and second cups.

9. The distraction system of claim 8, further comprising a radial bearing disposed annularly around an extension of the first cup.

10. The distraction system of claim 1, wherein the rotatable assembly is configured for rotation via a radial bearing at one end and a thrust bearing at another end.

11. The distraction system of claim 1, wherein the lead screw and the magnetic assembly are oriented along different axes.

12. The distraction system of claim 1, wherein the extension rod has a smaller diameter than the second portion of the adjustable portion.

13. The distraction system of claim 1, wherein the extension rod and the distraction rod are both configured for coupling with respective pedicle screws.

14. The distraction system of claim 1, wherein the lead screw is straight and interfaces with the distraction rod via a threaded nut.

15. The distraction system of claim 1, wherein the rotatable assembly comprises a motor.

16. The distraction system of claim 15, further comprising an implantable battery or an inductive coupler configured to power the motor.

17. A distraction system comprising:
an adjustable portion having a first portion separated from a second portion by an intermediate portion;
an extension rod extending from the second portion, wherein the extension rod includes a first end, a second end, and a hollow body extending between the first and second ends;
a distraction rod configured to telescope within the first portion;
a first rotatable assembly disposed within the second portion and coupled to a universal joint; and
a lead screw coupled to the universal joint and interfacing with the distraction rod,
wherein the distraction system is configured such that rotation of the rotatable assembly causes rotation of the universal joint which causes rotation of the lead screw, which causes the distraction rod to move relative to the adjustable portion,
wherein a curve of the adjustable portion defines an angle of 3° to 35° between the first portion and the second portion, and
wherein the curve of the adjustable portion defining the angle is permanent.

* * * * *